US010947512B2

(12) United States Patent
Peeples et al.

(10) Patent No.: US 10,947,512 B2
(45) Date of Patent: Mar. 16, 2021

(54) RESPIRATORY SYNCYTIAL VIRUS HAVING ALTERED NS1 PROTEIN FUNCTION AND RELATED MATERIALS AND METHODS

(71) Applicants: RESEARCH INSTITUTE AT NATIONWIDE CHILDREN'S HOSPITAL, Columbus, OH (US); UNIVERSITY OF SOUTH FLORIDA, Tampa, FL (US)

(72) Inventors: Mark Edward Peeples, Bexley, OH (US); Michael Nan-hao Teng, Tampa, FL (US); Octavio Ramilo, Columbus, OH (US); Maria Asuncion Mejias, Columbus, OH (US); Emilio Flano, Needham, MA (US)

(73) Assignees: Research Institute at Nationwide Children's Hospital, Columbus, OH (US); The University of South Florida, Tampa, FL (US)

( * ) Notice: Subject to any disclaimer, the term of this patent is extended or adjusted under 35 U.S.C. 154(b) by 0 days.

(21) Appl. No.: 15/752,548

(22) PCT Filed: Aug. 12, 2016

(86) PCT No.: PCT/US2016/046885
§ 371 (c)(1),
(2) Date: Feb. 13, 2018

(87) PCT Pub. No.: WO2017/030997
PCT Pub. Date: Feb. 23, 2017

(65) Prior Publication Data
US 2019/0169577 A1 Jun. 6, 2019

Related U.S. Application Data
(60) Provisional application No. 62/205,627, filed on Aug. 14, 2015.

(51) Int. Cl.
*A61K 39/155* (2006.01)
*C12N 7/04* (2006.01)
(Continued)

(52) U.S. Cl.
CPC .............. *C12N 7/00* (2013.01); *A61K 39/155* (2013.01); *C07K 14/005* (2013.01); *C12N 15/09* (2013.01);
(Continued)

(58) Field of Classification Search
None
See application file for complete search history.

(56) References Cited

U.S. PATENT DOCUMENTS

2015/0118732 A1 4/2015 Collins et al.

FOREIGN PATENT DOCUMENTS

| | | | |
|---|---|---|---|
| EP | 1085904 B1 | 11/2012 | |
| WO | 2001/081554 A1 | 11/2001 | |
| WO | WO-2010053883 A1 * | 5/2010 | ........... A61K 39/155 |

OTHER PUBLICATIONS

Baker et al., Protein Structure Predication and Structural Genomics, Science (2001) vol. 294, No. 5540, pp. 93-96 (Year: 2001).*
(Continued)

*Primary Examiner* — Michelle S Horning
(74) *Attorney, Agent, or Firm* — Faegre Drinker Biddle & Reath LLP

(57) ABSTRACT

Embodiments disclosed herein provide compositions, methods, and uses for respiratory syncytial viruses (RSV) and immunogenic compositions thereof. Certain embodiments provide RSV having a mutated NS1 protein, where the mutation causes the uncoupling of the NS1 protein's replication and type I interferon (IFN) antagonist functions. In some embodiments, this uncoupling can produce virions capable of inducing a strong, long-lasting innate immune
(Continued)

response while maintaining its ability to replicate in vitro. Also provided are methods for amplifying RSV in host cells, wherein amplified RSV has mutated NS1 protein in which the protein's replication and IFN antagonistic functions are uncoupled. In certain embodiments, the amplified RSV having mutated NS1 protein is formulated into immunogenic compositions, including vaccines. Other embodiments provide methods for inducing an effective immune response against RSV infection in a subject.

15 Claims, 7 Drawing Sheets

Specification includes a Sequence Listing.

(51) Int. Cl.

| | |
|---|---|
| ***C12N 15/00*** | (2006.01) |
| ***C12N 15/45*** | (2006.01) |
| ***C12N 5/10*** | (2006.01) |
| ***A61P 31/14*** | (2006.01) |
| ***C12N 7/00*** | (2006.01) |
| ***C12N 15/09*** | (2006.01) |
| ***C07K 14/005*** | (2006.01) |
| *A61K 39/12* | (2006.01) |
| *A61K 39/00* | (2006.01) |

(52) U.S. Cl.

CPC ...... *A61K 39/12* (2013.01); *A61K 2039/5254* (2013.01); *C12N 2760/18521* (2013.01); *C12N 2760/18534* (2013.01); *C12N 2760/18561* (2013.01)

(56) References Cited

OTHER PUBLICATIONS

Attwood, T. The Babel of Bioinformatics, Science (2000) vol. 290, No. 5491, pp. 471-473 (Year: 2000).*

International Search Report and Written Opinion issued in PCT/US2016/046885, dated Dec. 30, 2016, 13 pages.

Swedan et al. "Multiple Functional Domains and Complexes of the Two Nonstructural Proteins of Human Respiratory Syncytial Virus Contribute to interferon Suppression and Cellular Location," Journal of Virology, Jul. 27, 2011 (Jul. 27, 2011), vol. 85, No. 19, pp. 10090-10100. entire document.

Jin et al. "Recombinant Respiratory Syncytial Viruses with Deletions in the NS1, NS2, SH, and M2-2 Genes Are Attenuated in Vitro and in Vivo," Virology, Mar. 12, 2002 (Mar. 12, 2002), vol. 273, Iss. 1, pp. 210-218. entire document.

* cited by examiner

SEQUENCE LISTING

```
<160> NUMBER OF SEQ ID NOS: 29

<210> SEQ ID NO 1
<211> LENGTH: 139
<212> TYPE: PRT
<213> ORGANISM: Human respiratory syncytial virus
<220> FEATURE:
<221> NAME/KEY: misc_feature
<223> OTHER INFORMATION: NS1 protein sequence of human RSV strain A2

<400> SEQUENCE: 1

Met Gly Ser Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
            20                  25                  30

Lys Leu Ile His Leu Thr Asn Ala Leu Ala Lys Ala Val Ile His Thr
        35                  40                  45

Ile Lys Leu Asn Gly Ile Val Phe Val His Val Ile Thr Ser Ser Asp
    50                  55                  60

Ile Cys Pro Asn Asn Asn Ile Val Val Lys Ser Asn Phe Thr Thr Met
65                  70                  75                  80

Pro Val Leu Gln Asn Gly Gly Tyr Ile Trp Glu Met Met Glu Leu Thr
                85                  90                  95

His Cys Ser Gln Pro Asn Gly Leu Leu Asp Asp Asn Cys Glu Ile Lys
            100                 105                 110

Phe Ser Lys Lys Leu Ser Asp Ser Thr Met Thr Asn Tyr Met Asn Gln
        115                 120                 125

Leu Ser Glu Leu Leu Gly Phe Asp Leu Asn Pro
    130                 135


<210> SEQ ID NO 2
<211> LENGTH: 129
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant Nd10 (deletion of
      amino-terminal 10 aa)

<400> SEQUENCE: 2
```

```
Val Arg Leu Gln Asn Leu Phe Asp Asn Asp Glu Val Ala Leu Leu Lys
1               5                   10                  15

Ile Thr Cys Tyr Thr Asp Lys Leu Ile His Leu Thr Asn Ala Leu Ala
            20                  25                  30

Lys Ala Val Ile His Thr Ile Lys Leu Asn Gly Ile Val Phe Val His
        35                  40                  45

Val Ile Thr Ser Ser Asp Ile Cys Pro Asn Asn Asn Ile Val Val Lys
    50                  55                  60

Ser Asn Phe Thr Thr Met Pro Val Leu Gln Asn Gly Gly Tyr Ile Trp
65                  70                  75                  80

Glu Met Met Glu Leu Thr His Cys Ser Gln Pro Asn Gly Leu Leu Asp
                85                  90                  95

Asp Asn Cys Glu Ile Lys Phe Ser Lys Lys Leu Ser Asp Ser Thr Met
            100                 105                 110

Thr Asn Tyr Met Asn Gln Leu Ser Glu Leu Leu Gly Phe Asp Leu Asn
        115                 120                 125

Pro


<210> SEQ ID NO 3
<211> LENGTH: 129
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant Cd10 (deletion of
      carboxy-terminal 10 aa)

<400> SEQUENCE: 3

Met Gly Ser Asn Ser Leu Ser Met Ile Lys Val Arg Leu Gln Asn Leu
1               5                   10                  15

Phe Asp Asn Asp Glu Val Ala Leu Leu Lys Ile Thr Cys Tyr Thr Asp
            20                  25                  30

Lys Leu Ile His Leu Thr Asn Ala Leu Ala Lys Ala Val Ile His Thr
        35                  40                  45

Ile Lys Leu Asn Gly Ile Val Phe Val His Val Ile Thr Ser Ser Asp
    50                  55                  60

Ile Cys Pro Asn Asn Asn Ile Val Val Lys Ser Asn Phe Thr Thr Met
65                  70                  75                  80

Pro Val Leu Gln Asn Gly Gly Tyr Ile Trp Glu Met Met Glu Leu Thr
                85                  90                  95

His Cys Ser Gln Pro Asn Gly Leu Leu Asp Asp Asn Cys Glu Ile Lys
            100                 105                 110

Phe Ser Lys Lys Leu Ser Asp Ser Thr Met Thr Asn Tyr Met Asn Gln
        115                 120                 125

Leu


<210> SEQ ID NO 4
<211> LENGTH: 129
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d6-15 (deletion of aa
      6 through 15)

<400> SEQUENCE: 4

Met Gly Ser Asn Ser Leu Phe Asp Asn Asp Glu Val Ala Leu Leu Lys
1               5                   10                  15
```

Ile Thr Cys Tyr Thr Asp Lys Leu Ile His Leu Thr Asn Ala Leu Ala
20 25 30

Lys Ala Val Ile His Thr Ile Lys Leu Asn Gly Ile Val Phe Val His
35 40 45

Val Ile Thr Ser Ser Asp Ile Cys Pro Asn Asn Asn Ile Val Val Lys
50 55 60

Ser Asn Phe Thr Thr Met Pro Val Leu Gln Asn Gly Gly Tyr Ile Trp
65 70 75 80

Glu Met Met Glu Leu Thr His Cys Ser Gln Pro Asn Gly Leu Leu Asp
85 90 95

Asp Asn Cys Glu Ile Lys Phe Ser Lys Lys Leu Ser Asp Ser Thr Met
100 105 110

Thr Asn Tyr Met Asn Gln Leu Ser Glu Leu Leu Gly Phe Asp Leu Asn
115 120 125

Pro

<210> SEQ ID NO 5
<211> LENGTH: 126
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d6-18 (deltion of aa 6 through 18)

<400> SEQUENCE: 5

Met Gly Ser Asn Ser Asn Asp Glu Val Ala Leu Leu Lys Ile Thr Cys
1 5 10 15

Tyr Thr Asp Lys Leu Ile His Leu Thr Asn Ala Leu Ala Lys Ala Val
20 25 30

Ile His Thr Ile Lys Leu Asn Gly Ile Val Phe Val His Val Ile Thr
35 40 45

Ser Ser Asp Ile Cys Pro Asn Asn Asn Ile Val Val Lys Ser Asn Phe
50 55 60

Thr Thr Met Pro Val Leu Gln Asn Gly Gly Tyr Ile Trp Glu Met Met
65 70 75 80

Glu Leu Thr His Cys Ser Gln Pro Asn Gly Leu Leu Asp Asp Asn Cys
85 90 95

Glu Ile Lys Phe Ser Lys Lys Leu Ser Asp Ser Thr Met Thr Asn Tyr
100 105 110

Met Asn Gln Leu Ser Glu Leu Leu Gly Phe Asp Leu Asn Pro
115 120 125

<210> SEQ ID NO 6
<211> LENGTH: 128
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d8-18 (deletion of aa 8 through 18)

<400> SEQUENCE: 6

Met Gly Ser Asn Ser Leu Ser Asn Asp Glu Val Ala Leu Leu Lys Ile
1 5 10 15

Thr Cys Tyr Thr Asp Lys Leu Ile His Leu Thr Asn Ala Leu Ala Lys
20 25 30

Ala Val Ile His Thr Ile Lys Leu Asn Gly Ile Val Phe Val His Val

-continued 35 40 45

Ile Thr Ser Ser Asp Ile Cys Pro Asn Asn Asn Ile Val Val Lys Ser
50 55 60

Asn Phe Thr Thr Met Pro Val Leu Gln Asn Gly Gly Tyr Ile Trp Glu
65 70 75 80

Met Met Glu Leu Thr His Cys Ser Gln Pro Asn Gly Leu Leu Asp Asp
85 90 95

Asn Cys Glu Ile Lys Phe Ser Lys Lys Leu Ser Asp Ser Thr Met Thr
100 105 110

Asn Tyr Met Asn Gln Leu Ser Glu Leu Leu Gly Phe Asp Leu Asn Pro
115 120 125

<210> SEQ ID NO 7
<211> LENGTH: 126
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d8-20 (deletion of aa 8 through 20

<400> SEQUENCE: 7

Met Gly Ser Asn Ser Leu Ser Glu Val Ala Leu Leu Lys Ile Thr Cys
1 5 10 15

Tyr Thr Asp Lys Leu Ile His Leu Thr Asn Ala Leu Ala Lys Ala Val
20 25 30

Ile His Thr Ile Lys Leu Asn Gly Ile Val Phe Val His Val Ile Thr
35 40 45

Ser Ser Asp Ile Cys Pro Asn Asn Asn Ile Val Val Lys Ser Asn Phe
50 55 60

Thr Thr Met Pro Val Leu Gln Asn Gly Gly Tyr Ile Trp Glu Met Met
65 70 75 80

Glu Leu Thr His Cys Ser Gln Pro Asn Gly Leu Leu Asp Asp Asn Cys
85 90 95

Glu Ile Lys Phe Ser Lys Lys Leu Ser Asp Ser Thr Met Thr Asn Tyr
100 105 110

Met Asn Gln Leu Ser Glu Leu Leu Gly Phe Asp Leu Asn Pro
115 120 125

<210> SEQ ID NO 8
<211> LENGTH: 129
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d11-20 (deletion of aa 11 through 20)

<400> SEQUENCE: 8

Met Gly Ser Asn Ser Leu Ser Met Ile Lys Glu Val Ala Leu Leu Lys
1 5 10 15

Ile Thr Cys Tyr Thr Asp Lys Leu Ile His Leu Thr Asn Ala Leu Ala
20 25 30

Lys Ala Val Ile His Thr Ile Lys Leu Asn Gly Ile Val Phe Val His
35 40 45

Val Ile Thr Ser Ser Asp Ile Cys Pro Asn Asn Asn Ile Val Val Lys
50 55 60

Ser Asn Phe Thr Thr Met Pro Val Leu Gln Asn Gly Gly Tyr Ile Trp
65 70 75 80

-continued

```
Glu Met Met Glu Leu Thr His Cys Ser Gln Pro Asn Gly Leu Leu Asp
                85                  90                  95

Asp Asn Cys Glu Ile Lys Phe Ser Lys Lys Leu Ser Asp Ser Thr Met
            100                 105                 110

Thr Asn Tyr Met Asn Gln Leu Ser Glu Leu Leu Gly Phe Asp Leu Asn
        115                 120                 125

Pro


<210> SEQ ID NO 9
<211> LENGTH: 128
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d6-10,12,15-19
      (deletion of aa 6 through 10, 12, and 15 through 19)

<400> SEQUENCE: 9

Met Gly Ser Asn Ser Val Leu Gln Asp Glu Val Ala Leu Leu Lys Ile
1               5                   10                  15

Thr Cys Tyr Thr Asp Lys Leu Ile His Leu Thr Asn Ala Leu Ala Lys
            20                  25                  30

Ala Val Ile His Thr Ile Lys Leu Asn Gly Ile Val Phe Val His Val
        35                  40                  45

Ile Thr Ser Ser Asp Ile Cys Pro Asn Asn Asn Ile Val Val Lys Ser
    50                  55                  60

Asn Phe Thr Thr Met Pro Val Leu Gln Asn Gly Gly Tyr Ile Trp Glu
65                  70                  75                  80

Met Met Glu Leu Thr His Cys Ser Gln Pro Asn Gly Leu Leu Asp Asp
                85                  90                  95

Asn Cys Glu Ile Lys Phe Ser Lys Lys Leu Ser Asp Ser Thr Met Thr
            100                 105                 110

Asn Tyr Met Asn Gln Leu Ser Glu Leu Leu Gly Phe Asp Leu Asn Pro
        115                 120                 125


<210> SEQ ID NO 10
<211> LENGTH: 134
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant Nd5 (deletion of aa 1
      through 5)

<400> SEQUENCE: 10

Leu Ser Met Ile Lys Val Arg Leu Gln Asn Leu Phe Asp Asn Asp Glu
1               5                   10                  15

Val Ala Leu Leu Lys Ile Thr Cys Tyr Thr Asp Lys Leu Ile His Leu
            20                  25                  30

Thr Asn Ala Leu Ala Lys Ala Val Ile His Thr Ile Lys Leu Asn Gly
        35                  40                  45

Ile Val Phe Val His Val Ile Thr Ser Ser Asp Ile Cys Pro Asn Asn
    50                  55                  60

Asn Ile Val Val Lys Ser Asn Phe Thr Thr Met Pro Val Leu Gln Asn
65                  70                  75                  80

Gly Gly Tyr Ile Trp Glu Met Met Glu Leu Thr His Cys Ser Gln Pro
                85                  90                  95

Asn Gly Leu Leu Asp Asp Asn Cys Glu Ile Lys Phe Ser Lys Lys Leu
```

-continued 100 105 110

Ser Asp Ser Thr Met Thr Asn Tyr Met Asn Gln Leu Ser Glu Leu Leu
115 120 125

Gly Phe Asp Leu Asn Pro
130

<210> SEQ ID NO 11
<211> LENGTH: 135
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d2-5 (deletion of aa 2 through 5

<400> SEQUENCE: 11

Met Leu Ser Met Ile Lys Val Arg Leu Gln Asn Leu Phe Asp Asn Asp
1 5 10 15

Glu Val Ala Leu Leu Lys Ile Thr Cys Tyr Thr Asp Lys Leu Ile His
20 25 30

Leu Thr Asn Ala Leu Ala Lys Ala Val Ile His Thr Ile Lys Leu Asn
35 40 45

Gly Ile Val Phe Val His Val Ile Thr Ser Ser Asp Ile Cys Pro Asn
50 55 60

Asn Asn Ile Val Val Lys Ser Asn Phe Thr Thr Met Pro Val Leu Gln
65 70 75 80

Asn Gly Gly Tyr Ile Trp Glu Met Met Glu Leu Thr His Cys Ser Gln
85 90 95

Pro Asn Gly Leu Leu Asp Asp Asn Cys Glu Ile Lys Phe Ser Lys Lys
100 105 110

Leu Ser Asp Ser Thr Met Thr Asn Tyr Met Asn Gln Leu Ser Glu Leu
115 120 125

Leu Gly Phe Asp Leu Asn Pro
130 135

<210> SEQ ID NO 12
<211> LENGTH: 133
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d2-7 (deletion of aa 2 through 7)

<400> SEQUENCE: 12

Met Met Ile Lys Val Arg Leu Gln Asn Leu Phe Asp Asn Asp Glu Val
1 5 10 15

Ala Leu Leu Lys Ile Thr Cys Tyr Thr Asp Lys Leu Ile His Leu Thr
20 25 30

Asn Ala Leu Ala Lys Ala Val Ile His Thr Ile Lys Leu Asn Gly Ile
35 40 45

Val Phe Val His Val Ile Thr Ser Ser Asp Ile Cys Pro Asn Asn Asn
50 55 60

Ile Val Val Lys Ser Asn Phe Thr Thr Met Pro Val Leu Gln Asn Gly
65 70 75 80

Gly Tyr Ile Trp Glu Met Met Glu Leu Thr His Cys Ser Gln Pro Asn
85 90 95

Gly Leu Leu Asp Asp Asn Cys Glu Ile Lys Phe Ser Lys Lys Leu Ser
100 105 110

-continued

```
Asp Ser Thr Met Thr Asn Tyr Met Asn Gln Leu Ser Glu Leu Leu Gly
        115                 120                 125

Phe Asp Leu Asn Pro
    130


<210> SEQ ID NO 13
<211> LENGTH: 136
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d5-7 (deletion of aa 5
      through 7)

<400> SEQUENCE: 13

Met Gly Ser Asn Met Ile Lys Val Arg Leu Gln Asn Leu Phe Asp Asn
1               5                   10                  15

Asp Glu Val Ala Leu Leu Lys Ile Thr Cys Tyr Thr Asp Lys Leu Ile
            20                  25                  30

His Leu Thr Asn Ala Leu Ala Lys Ala Val Ile His Thr Ile Lys Leu
        35                  40                  45

Asn Gly Ile Val Phe Val His Val Ile Thr Ser Ser Asp Ile Cys Pro
    50                  55                  60

Asn Asn Asn Ile Val Val Lys Ser Asn Phe Thr Thr Met Pro Val Leu
65                  70                  75                  80

Gln Asn Gly Gly Tyr Ile Trp Glu Met Met Glu Leu Thr His Cys Ser
                85                  90                  95

Gln Pro Asn Gly Leu Leu Asp Asp Asn Cys Glu Ile Lys Phe Ser Lys
            100                 105                 110

Lys Leu Ser Asp Ser Thr Met Thr Asn Tyr Met Asn Gln Leu Ser Glu
        115                 120                 125

Leu Leu Gly Phe Asp Leu Asn Pro
    130                 135


<210> SEQ ID NO 14
<211> LENGTH: 134
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d6-10 (deletion of aa
      6 through 10)

<400> SEQUENCE: 14

Met Gly Ser Asn Ser Val Arg Leu Gln Asn Leu Phe Asp Asn Asp Glu
1               5                   10                  15

Val Ala Leu Leu Lys Ile Thr Cys Tyr Thr Asp Lys Leu Ile His Leu
            20                  25                  30

Thr Asn Ala Leu Ala Lys Ala Val Ile His Thr Ile Lys Leu Asn Gly
        35                  40                  45

Ile Val Phe Val His Val Ile Thr Ser Ser Asp Ile Cys Pro Asn Asn
    50                  55                  60

Asn Ile Val Val Lys Ser Asn Phe Thr Thr Met Pro Val Leu Gln Asn
65                  70                  75                  80

Gly Gly Tyr Ile Trp Glu Met Met Glu Leu Thr His Cys Ser Gln Pro
                85                  90                  95

Asn Gly Leu Leu Asp Asp Asn Cys Glu Ile Lys Phe Ser Lys Lys Leu
            100                 105                 110
```

```
Ser Asp Ser Thr Met Thr Asn Tyr Met Asn Gln Leu Ser Glu Leu Leu
        115                 120                 125

Gly Phe Asp Leu Asn Pro
    130


<210> SEQ ID NO 15
<211> LENGTH: 134
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d11-15 (deletion of aa
      11 through 15)

<400> SEQUENCE: 15

Met Gly Ser Asn Ser Leu Ser Met Ile Lys Leu Phe Asp Asn Asp Glu
1               5                   10                  15

Val Ala Leu Leu Lys Ile Thr Cys Tyr Thr Asp Lys Leu Ile His Leu
            20                  25                  30

Thr Asn Ala Leu Ala Lys Ala Val Ile His Thr Ile Lys Leu Asn Gly
        35                  40                  45

Ile Val Phe Val His Val Ile Thr Ser Ser Asp Ile Cys Pro Asn Asn
    50                  55                  60

Asn Ile Val Val Lys Ser Asn Phe Thr Thr Met Pro Val Leu Gln Asn
65                  70                  75                  80

Gly Gly Tyr Ile Trp Glu Met Met Glu Leu Thr His Cys Ser Gln Pro
                85                  90                  95

Asn Gly Leu Leu Asp Asp Asn Cys Glu Ile Lys Phe Ser Lys Lys Leu
            100                 105                 110

Ser Asp Ser Thr Met Thr Asn Tyr Met Asn Gln Leu Ser Glu Leu Leu
        115                 120                 125

Gly Phe Asp Leu Asn Pro
    130


<210> SEQ ID NO 16
<211> LENGTH: 134
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d16-20 (deletion of aa
      16 through 20)

<400> SEQUENCE: 16

Met Gly Ser Asn Ser Leu Ser Met Ile Lys Val Arg Leu Gln Asn Glu
1               5                   10                  15

Val Ala Leu Leu Lys Ile Thr Cys Tyr Thr Asp Lys Leu Ile His Leu
            20                  25                  30

Thr Asn Ala Leu Ala Lys Ala Val Ile His Thr Ile Lys Leu Asn Gly
        35                  40                  45

Ile Val Phe Val His Val Ile Thr Ser Ser Asp Ile Cys Pro Asn Asn
    50                  55                  60

Asn Ile Val Val Lys Ser Asn Phe Thr Thr Met Pro Val Leu Gln Asn
65                  70                  75                  80

Gly Gly Tyr Ile Trp Glu Met Met Glu Leu Thr His Cys Ser Gln Pro
                85                  90                  95

Asn Gly Leu Leu Asp Asp Asn Cys Glu Ile Lys Phe Ser Lys Lys Leu
            100                 105                 110

Ser Asp Ser Thr Met Thr Asn Tyr Met Asn Gln Leu Ser Glu Leu Leu
```

-continued 115 120 125

Gly Phe Asp Leu Asn Pro
130

<210> SEQ ID NO 17
<211> LENGTH: 133
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d11-13,18-20 (deletion of aa 11 through 13 and 18 through 20)

<400> SEQUENCE: 17

Met Gly Ser Asn Ser Leu Ser Met Ile Lys Gln Asn Leu Phe Glu Val
1 5 10 15

Ala Leu Leu Lys Ile Thr Cys Tyr Thr Asp Lys Leu Ile His Leu Thr
20 25 30

Asn Ala Leu Ala Lys Ala Val Ile His Thr Ile Lys Leu Asn Gly Ile
35 40 45

Val Phe Val His Val Ile Thr Ser Ser Asp Ile Cys Pro Asn Asn Asn
50 55 60

Ile Val Val Lys Ser Asn Phe Thr Thr Met Pro Val Leu Gln Asn Gly
65 70 75 80

Gly Tyr Ile Trp Glu Met Met Glu Leu Thr His Cys Ser Gln Pro Asn
85 90 95

Gly Leu Leu Asp Asp Asn Cys Glu Ile Lys Phe Ser Lys Lys Leu Ser
100 105 110

Asp Ser Thr Met Thr Asn Tyr Met Asn Gln Leu Ser Glu Leu Leu Gly
115 120 125

Phe Asp Leu Asn Pro
130

<210> SEQ ID NO 18
<211> LENGTH: 134
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant Cd5 (deletion of aa 135-139)

<400> SEQUENCE: 18

Met Gly Ser Asn Ser Leu Ser Met Ile Lys Val Arg Leu Gln Asn Leu
1 5 10 15

Phe Asp Asn Asp Glu Val Ala Leu Leu Lys Ile Thr Cys Tyr Thr Asp
20 25 30

Lys Leu Ile His Leu Thr Asn Ala Leu Ala Lys Ala Val Ile His Thr
35 40 45

Ile Lys Leu Asn Gly Ile Val Phe Val His Val Ile Thr Ser Ser Asp
50 55 60

Ile Cys Pro Asn Asn Asn Ile Val Val Lys Ser Asn Phe Thr Thr Met
65 70 75 80

Pro Val Leu Gln Asn Gly Gly Tyr Ile Trp Glu Met Met Glu Leu Thr
85 90 95

His Cys Ser Gln Pro Asn Gly Leu Leu Asp Asp Asn Cys Glu Ile Lys
100 105 110

Phe Ser Lys Lys Leu Ser Asp Ser Thr Met Thr Asn Tyr Met Asn Gln
115 120 125

-continued

```
Leu Ser Glu Leu Leu Gly
    130


<210> SEQ ID NO 19
<211> LENGTH: 138
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d9 (deletion of aa 9)

<400> SEQUENCE: 19

Met Gly Ser Asn Ser Leu Ser Met Lys Val Arg Leu Gln Asn Leu Phe
1               5                   10                  15

Asp Asn Asp Glu Val Ala Leu Leu Lys Ile Thr Cys Tyr Thr Asp Lys
            20                  25                  30

Leu Ile His Leu Thr Asn Ala Leu Ala Lys Ala Val Ile His Thr Ile
        35                  40                  45

Lys Leu Asn Gly Ile Val Phe Val His Val Ile Thr Ser Ser Asp Ile
    50                  55                  60

Cys Pro Asn Asn Asn Ile Val Val Lys Ser Asn Phe Thr Thr Met Pro
65                  70                  75                  80

Val Leu Gln Asn Gly Gly Tyr Ile Trp Glu Met Met Glu Leu Thr His
                85                  90                  95

Cys Ser Gln Pro Asn Gly Leu Leu Asp Asp Asn Cys Glu Ile Lys Phe
            100                 105                 110

Ser Lys Lys Leu Ser Asp Ser Thr Met Thr Asn Tyr Met Asn Gln Leu
        115                 120                 125

Ser Glu Leu Leu Gly Phe Asp Leu Asn Pro
    130                 135


<210> SEQ ID NO 20
<211> LENGTH: 138
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d11 (deletion of aa
      11)

<400> SEQUENCE: 20

Met Gly Ser Asn Ser Leu Ser Met Ile Lys Arg Leu Gln Asn Leu Phe
1               5                   10                  15

Asp Asn Asp Glu Val Ala Leu Leu Lys Ile Thr Cys Tyr Thr Asp Lys
            20                  25                  30

Leu Ile His Leu Thr Asn Ala Leu Ala Lys Ala Val Ile His Thr Ile
        35                  40                  45

Lys Leu Asn Gly Ile Val Phe Val His Val Ile Thr Ser Ser Asp Ile
    50                  55                  60

Cys Pro Asn Asn Asn Ile Val Val Lys Ser Asn Phe Thr Thr Met Pro
65                  70                  75                  80

Val Leu Gln Asn Gly Gly Tyr Ile Trp Glu Met Met Glu Leu Thr His
                85                  90                  95

Cys Ser Gln Pro Asn Gly Leu Leu Asp Asp Asn Cys Glu Ile Lys Phe
            100                 105                 110

Ser Lys Lys Leu Ser Asp Ser Thr Met Thr Asn Tyr Met Asn Gln Leu
        115                 120                 125

Ser Glu Leu Leu Gly Phe Asp Leu Asn Pro
```

-continued

```
130                 135


<210> SEQ ID NO 21
<211> LENGTH: 138
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d12 (deletion of aa
      12)

<400> SEQUENCE: 21

Met Gly Ser Asn Ser Leu Ser Met Ile Lys Val Leu Gln Asn Leu Phe
1               5                   10                  15

Asp Asn Asp Glu Val Ala Leu Leu Lys Ile Thr Cys Tyr Thr Asp Lys
            20                  25                  30

Leu Ile His Leu Thr Asn Ala Leu Ala Lys Ala Val Ile His Thr Ile
        35                  40                  45

Lys Leu Asn Gly Ile Val Phe Val His Val Ile Thr Ser Ser Asp Ile
    50                  55                  60

Cys Pro Asn Asn Asn Ile Val Val Lys Ser Asn Phe Thr Thr Met Pro
65                  70                  75                  80

Val Leu Gln Asn Gly Gly Tyr Ile Trp Glu Met Met Glu Leu Thr His
                85                  90                  95

Cys Ser Gln Pro Asn Gly Leu Leu Asp Asp Asn Cys Glu Ile Lys Phe
            100                 105                 110

Ser Lys Lys Leu Ser Asp Ser Thr Met Thr Asn Tyr Met Asn Gln Leu
        115                 120                 125

Ser Glu Leu Leu Gly Phe Asp Leu Asn Pro
    130                 135


<210> SEQ ID NO 22
<211> LENGTH: 138
<212> TYPE: PRT
<213> ORGANISM: Artificial Sequence
<220> FEATURE:
<223> OTHER INFORMATION: Artificial sequence based on human RSV NS1
      protein (SEQ ID NO: 1); NS1 deletion mutant d13 (deletion of aa
      13)

<400> SEQUENCE: 22

Met Gly Ser Asn Ser Leu Ser Met Ile Lys Val Arg Gln Asn Leu Phe
1               5                   10                  15

Asp Asn Asp Glu Val Ala Leu Leu Lys Ile Thr Cys Tyr Thr Asp Lys
            20                  25                  30

Leu Ile His Leu Thr Asn Ala Leu Ala Lys Ala Val Ile His Thr Ile
        35                  40                  45

Lys Leu Asn Gly Ile Val Phe Val His Val Ile Thr Ser Ser Asp Ile
    50                  55                  60

Cys Pro Asn Asn Asn Ile Val Val Lys Ser Asn Phe Thr Thr Met Pro
65                  70                  75                  80

Val Leu Gln Asn Gly Gly Tyr Ile Trp Glu Met Met Glu Leu Thr His
                85                  90                  95

Cys Ser Gln Pro Asn Gly Leu Leu Asp Asp Asn Cys Glu Ile Lys Phe
            100                 105                 110

Ser Lys Lys Leu Ser Asp Ser Thr Met Thr Asn Tyr Met Asn Gln Leu
        115                 120                 125

Ser Glu Leu Leu Gly Phe Asp Leu Asn Pro
    130                 135
```

<210> SEQ ID NO 23
<211> LENGTH: 137
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d7,8 (deletion of aa 7 and 8)

<400> SEQUENCE: 23

```
Met Gly Ser Asn Ser Leu Ile Lys Val Arg Leu Gln Asn Leu Phe Asp
1               5                   10                  15

Asn Asp Glu Val Ala Leu Leu Lys Ile Thr Cys Tyr Thr Asp Lys Leu
            20                  25                  30

Ile His Leu Thr Asn Ala Leu Ala Lys Ala Val Ile His Thr Ile Lys
        35                  40                  45

Leu Asn Gly Ile Val Phe Val His Val Ile Thr Ser Ser Asp Ile Cys
    50                  55                  60

Pro Asn Asn Asn Ile Val Val Lys Ser Asn Phe Thr Thr Met Pro Val
65                  70                  75                  80

Leu Gln Asn Gly Gly Tyr Ile Trp Glu Met Met Glu Leu Thr His Cys
                85                  90                  95

Ser Gln Pro Asn Gly Leu Leu Asp Asp Asn Cys Glu Ile Lys Phe Ser
            100                 105                 110

Lys Lys Leu Ser Asp Ser Thr Met Thr Asn Tyr Met Asn Gln Leu Ser
        115                 120                 125

Glu Leu Leu Gly Phe Asp Leu Asn Pro
    130                 135
```

<210> SEQ ID NO 24
<211> LENGTH: 136
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d9-11 (deletion of aa 9, 10, and 11)

<400> SEQUENCE: 24

```
Met Gly Ser Asn Ser Leu Ser Met Arg Leu Gln Asn Leu Phe Asp Asn
1               5                   10                  15

Asp Glu Val Ala Leu Leu Lys Ile Thr Cys Tyr Thr Asp Lys Leu Ile
            20                  25                  30

His Leu Thr Asn Ala Leu Ala Lys Ala Val Ile His Thr Ile Lys Leu
        35                  40                  45

Asn Gly Ile Val Phe Val His Val Ile Thr Ser Ser Asp Ile Cys Pro
    50                  55                  60

Asn Asn Asn Ile Val Val Lys Ser Asn Phe Thr Thr Met Pro Val Leu
65                  70                  75                  80

Gln Asn Gly Gly Tyr Ile Trp Glu Met Met Glu Leu Thr His Cys Ser
                85                  90                  95

Gln Pro Asn Gly Leu Leu Asp Asp Asn Cys Glu Ile Lys Phe Ser Lys
            100                 105                 110

Lys Leu Ser Asp Ser Thr Met Thr Asn Tyr Met Asn Gln Leu Ser Glu
        115                 120                 125

Leu Leu Gly Phe Asp Leu Asn Pro
    130                 135
```

<210> SEQ ID NO 25
<211> LENGTH: 137
<212> TYPE: PRT
<213> ORGANISM: Artificial Sequence
<220> FEATURE:
<223> OTHER INFORMATION: Artificial sequence based on human RSV NS1 protein (SEQ ID NO: 1); NS1 deletion mutant d9,12 (deletion of aa 9 and 12)

<400> SEQUENCE: 25

```
Met Gly Ser Asn Ser Leu Ser Met Lys Val Leu Gln Asn Leu Phe Asp
1               5                   10                  15

Asn Asp Glu Val Ala Leu Leu Lys Ile Thr Cys Tyr Thr Asp Lys Leu
            20                  25                  30

Ile His Leu Thr Asn Ala Leu Ala Lys Ala Val Ile His Thr Ile Lys
        35                  40                  45

Leu Asn Gly Ile Val Phe Val His Val Ile Thr Ser Ser Asp Ile Cys
    50                  55                  60

Pro Asn Asn Asn Ile Val Val Lys Ser Asn Phe Thr Thr Met Pro Val
65                  70                  75                  80

Leu Gln Asn Gly Gly Tyr Ile Trp Glu Met Met Glu Leu Thr His Cys
                85                  90                  95

Ser Gln Pro Asn Gly Leu Leu Asp Asp Asn Cys Glu Ile Lys Phe Ser
            100                 105                 110

Lys Lys Leu Ser Asp Ser Thr Met Thr Asn Tyr Met Asn Gln Leu Ser
        115                 120                 125

Glu Leu Leu Gly Phe Asp Leu Asn Pro
    130                 135
```

<210> SEQ ID NO 26
<211> LENGTH: 21
<212> TYPE: DNA
<213> ORGANISM: Artificial Sequence
<220> FEATURE:
<223> OTHER INFORMATION: Synthetic primer

<400> SEQUENCE: 26
ctaactgcaa cctttcgaag c 21

<210> SEQ ID NO 27
<211> LENGTH: 22
<212> TYPE: DNA
<213> ORGANISM: Artificial Sequence
<220> FEATURE:
<223> OTHER INFORMATION: Synthtetic primer

<400> SEQUENCE: 27
ggaaagagct gtagtggaga ag 22

<210> SEQ ID NO 28
<211> LENGTH: 20
<212> TYPE: DNA
<213> ORGANISM: Artificial Sequence
<220> FEATURE:
<223> OTHER INFORMATION: Synthetic primer

<400> SEQUENCE: 28
gtaacccgtt gaaccccatt 20

<210> SEQ ID NO 29
<211> LENGTH: 20
<212> TYPE: DNA

-continued

```
<213> ORGANISM: Artificial Sequence
<220> FEATURE:
<223> OTHER INFORMATION: Synthetic primer

<400> SEQUENCE: 29

ccatccaatc ggtagtagcg                                                20
```

RESPIRATORY SYNCYTIAL VIRUS HAVING ALTERED NS1 PROTEIN FUNCTION AND RELATED MATERIALS AND METHODS

CROSS REFERENCE TO RELATED APPLICATIONS

This application is a U.S. National Stage Application under 35 U.S.C. § 371 of International Application No. PCT/US2016/046885, filed on Aug. 12, 2016, which claims the benefit of U.S. Provisional Patent Application No. 62/205,627, filed on Aug. 14, 2015, the disclosures of each of which are incorporated herein by reference in their entireties.

FIELD

Embodiments disclosed herein provide for compositions, methods, and uses of respiratory syncytial viruses (RSV) and immunogenic compositions thereof. Certain embodiments concern RSV having a mutated NS1 protein, where the mutation causes uncoupling of the NS1 protein's replication and type I interferon (IFN) antagonist functions. In some embodiments, this uncoupling can produce virions capable of inducing a strong, long-lasting innate immune response in a subject while maintaining its ability to replicate in vitro. Other embodiments provide methods for amplifying mutated RSV in host cells. In certain embodiments, amplified RSV having mutated NS1 proteins can be formulated into immunogenic compositions against RSV, such as vaccines. Other embodiments provide compositions for use in methods for inducing an effective immune response against RSV infection in a subject.

SEQUENCE LISTING

The instant application contains a Sequence Listing which has been submitted via EFS-web in ASCII format and is hereby incorporated by reference in its entirety. The ASCII copy, created on Aug. 12, 2016, is named 509892.10 Sequence Listing_ST25, and is 35,098 bytes in size. A substitute sequence listing has been submitted via EFS-web in ASCII format and is hereby incorporated by reference in its entirety. The substitute ASCII file, created on Dec. 17, 2018, is named 509892 14 Replacement Sequence_Listing_ST25.txt, and is 35,218 bytes in size.

BACKGROUND

First discovered in 1956 as a lower respiratory tract pathogen of children in their first year of life, human respiratory syncytial virus (RSV) is an enveloped, negative-sense single-stranded RNA virus belonging to the *Pneumovirus* genus within the Pneumovirinae subfamily of the family Paramyxoviridae. RSV is a major cause of lower respiratory tract infections, most commonly resulting in mild respiratory tract disease. However, infection with hRSV may result in severe bronchiolitis and pneumonia. In industrialized countries, RSV accounts for up to 70% of hospitalized bronchiolitis cases. Among infectious agents, RSV is the second leading cause of death in infants under one year of age. Worldwide, in 2010 alone, RSV is estimated to have caused over 230,000 deaths in children under 5 years of age, with the majority of deaths being in infants under the age of one (Lozano et al., Lancet (2012.) 380:2095-2128).

Currently, only supportive care is available to treat individuals infected with lower respiratory tract disease. A humanized neutralizing monoclonal antibody (mAb), palivizumab, can be used prophylactically, but is only used on infants and children considered at greatest risk for severe disease.

In the 1960s, a formalin-inactivated RSV vaccine was tested in infants and young children. Instead of protecting the airways of the infants upon natural infection, 80% of the vaccinated infants were hospitalized and two infants succumbed, while only 5% of the control vaccinated infants were hospitalized (Kim et al., Am J Epidemiol (1969) 89:422-434). As a result, the focus shifted to live attenuated viral vaccines for protection and a great deal of effort has been spent developing these vaccines (Crowe et al., Vaccine (1995) 13:847-855; Karron et al., J Infect Dis (2005) 191: 1093-1104; Karron et al., J Infect Dis (1997) 176:1428-1436; Kim et al., Pediatrics (1971) 48:745-755; Malkin et al., PLoS One (2013) 8:e77104; Wright et al., J Infect Dis (2000) 182:1331-1342; Wright et al., J Infect Dis (2006) 193:573-581).

SUMMARY

Embodiments disclosed herein provide compositions, methods, and uses for modified respiratory syncytial viruses (RSV) and immunogenic compositions thereof. Certain embodiments provide RSV having a mutated NS1 protein in which the NS1 protein's replication function is retained, but the NS1 protein's Type I interferon (IFN) antagonistic activity is reduced or eliminated. In some embodiments, an RSV expresses mutated NS1 protein whose IFN antagonistic activities are reduced relative to an RSV having a wild-type NS1 protein without reducing the NS1 protein's ability to support RSV replication relative to RSV lacking NS1 (RSV ΔNS1). In other embodiments, methods for amplifying RSV in host cells are disclosed, where the amplified RSV have mutated NS1 proteins in which the protein's replication and IFN antagonistic functions are uncoupled. In certain embodiments, the amplified RSV having mutated NS1 proteins can be formulated into an immunogenic composition for use against RSV, for example, a vaccine for reducing or preventing RSV infection. Other embodiments provide compositions for use in methods for inducing an effective immune response against RSV infection in a subject.

In some embodiments, a modified RSV can have a mutated NS1 protein where the protein's replication function is uncoupled from its IFN antagonistic function, allowing for the efficient replication of RSV in vitro, and producing virions capable of causing strong, long lasting innate immune reactions. In accordance with these embodiments, the RSV having the mutated NS1 protein exhibits increased replication relative to an RSV lacking the NS1 gene (RSV ΔNS1) and reduced IFN antagonism relative to an RSV having a wild-type NS1 protein. In some embodiments, the NS1 protein is mutated relative to an RSV NS1 protein represented by the polypeptide sequence of SEQ ID NO: 1. In some embodiments, the NS1 comprises one or more deletion mutations that result in the uncoupling of the protein's replication and IFN antagonistic functions. For example, in some embodiments, mutation of NS1 can be a deletion of 10 or more amino acids of the first 20 amino acids of the amino-terminus of an NS1 protein having at least 95% sequence identity with SEQ ID NO: 1, a deletion of 10 amino acids of the carboxy-terminus of an NS1 protein having at least 95% sequence identity with SEQ ID NO: 1, or a deletion of 1 to 5 amino acids in the first 20 amino acids of the amino-terminus of the NS1 protein having at least 95% sequence identity with SEQ ID NO: 1. In accordance with these embodiments, the deletion mutations can be of consecutive or non-consecutive amino acids.

In certain embodiments, deletion mutations of NS1 of RSV as disclosed herein can be selected from the from the group consisting of NΔ10; CΔ10; Δ6-15; Δ6-18; Δ8-18; Δ8-20; Δ6-10,12,15-19; NΔ5; Δ2-5; Δ2-7; Δ5-7; Δ6-10; Δ11-15; Δ11-13,18-20; Δ9; Δ11; Δ12; Δ13; Δ7,8; Δ9-11; and Δ9,12 where NS1 has at least 95% sequence identity with SEQ ID NO: 1. In other embodiments, deletion mutations can be selected from the group consisting of NΔ10; NΔ11-20; Δ6-10; Δ16-20; Δ11; and Δ9,11 relative to an RSV NS1 protein having at least 95% sequence identity with SEQ ID NO: 1.

In some embodiments, the RSV having a mutated NS1 protein is attenuated.

Other embodiments disclosed herein provide methods for producing an immunogenic composition against RSV where the immunogenic composition can include, but is not limited to, an RSV having a mutated NS1 protein, where the mutation uncouples the NS1 protein's replication and IFN antagonistic functions. In other embodiments, methods can include having a host cell culture and inoculating the host cell culture with an RSV described herein having a mutated NS1 protein, incubating the host cell culture with the RSV, harvesting the RSV from the host cell culture following a period of incubation, and formulating the harvested RSV into an immunogenic composition of use against RSV infection. Some embodiments can further include purifying the harvested mutated RSV.

In some embodiments, formulating steps can include combining the harvested RSV with a pharmaceutically acceptable carrier, vehicle, or excipient, an adjuvant, or a combination thereof to generate a pharmaceutical composition. In certain embodiments, immunogenic compositions against RSV of embodiments disclosed herein can be a pharmaceutical composition where the immunogenic composition includes a pharmaceutically acceptable carrier, vehicle, excipient, or combination thereof. In other embodiments, a pharmaceutically acceptable immunogenic composition against mutated RSV can include an adjuvant for further induction of the immune system in a subject when administered.

Other embodiments provide methods for inducing an immune response against RSV infection in a subject. In some embodiments, the methods can include administering to the subject an immunologically effective dose of an immunogenic composition disclosed herein against RSV. In some embodiments, the subject can be a human. In other embodiments, the subject can be a human infant or child. In other embodiment, an immunogenic composition against RSV can be administered via any known route of administration. In accordance with this embodiment, a route of administration can be but is not limited to, intranasal administration, subcutaneous administration, intramuscular administration, intradermal administration, and oral administration. In some embodiments, at least one additional dose of an immunogenic composition against RSV can be administered to the subject.

DEFINITIONS

Figure 1A:
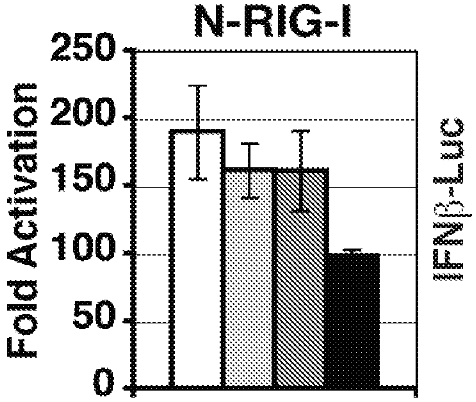
FIGS. 1A-1D are exemplary bar graphs representing inhibition of N-RIG-I and TRIF-induced IFN activation. HEK293T cells were transfected with expression plasmids encoding NS1 and N-RIG-I (FIGS. 1A-1B) or TRIF (FIGS. 1C-1D) plus luciferase reporter constructs under the control of the IFNβ (FIGS. 1A and 1C) or ISG56 (FIGS. 1B and 1D) promoter.
Figure 1B:
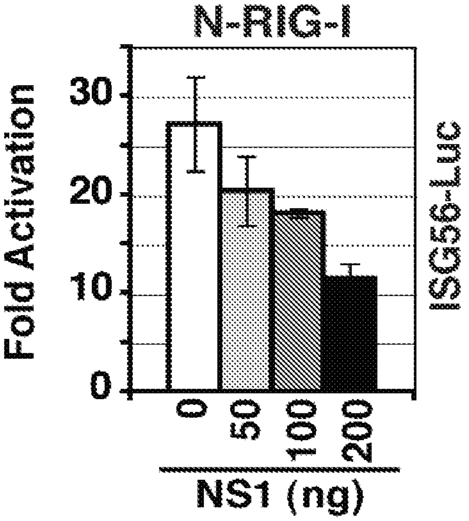
Figure 1C:
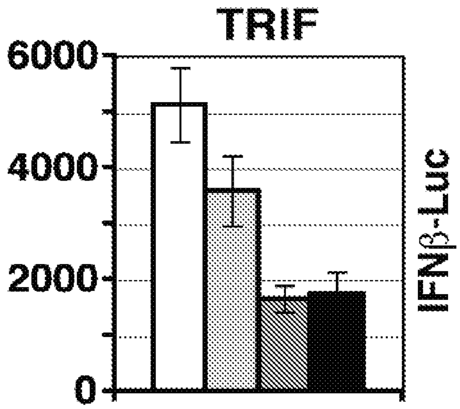
Figure 1D:
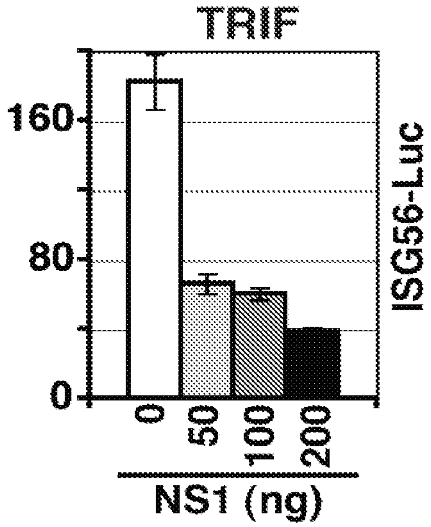

An "immunogenic composition" can be any mixture, aqueous solution, non-aqueous solution, suspension, emulsion, gel, or the like, including an RSV of an embodiment described herein and at least one other component. The RSV can be a live RSV or a live, attenuated RSV. Other components can be, for example, one or more pharmaceutical agents, carriers, vehicles, excipients, or a combination thereof. Generally, immunogenic compositions can be prepared by uniformly combining the live attenuated virus with a liquid carrier, vehicle, or excipient, or a finely divided solid carrier, vehicle, or excipient, or combination thereof. The immunogenic composition includes enough immunogenic virus to produce an effective immune response. Accordingly, the immunogenic compositions described herein encompass any composition made by admixing a compound of mutant RSV described herein or RSV amplified using a method described herein and a pharmaceutically acceptable carrier, vehicle, or excipient. By "pharmaceutically acceptable" it is meant that the carrier, vehicle, or excipient must be compatible with the other ingredients of the formulation and not deleterious to the recipient thereof.

As used herein, the term "effective immune response" refers to an immune response that confers immunity against an infection or reduces the probability of infection recurrence. For instance, an immune response can be considered to be an "effective immune response" if it is sufficient to prevent a subject from developing a respiratory syncytial virus (RSV) infection or a lower respiratory tract RSV infection after administration of a challenge dose of RSV. An effective immune response can include a cell mediated immune response, and/or a humoral immune response.

The term "immunologically effective dose" can be an amount of a vaccine or immunogenic composition of the present disclosure sufficient to cause an effective immune response. The immunologically effective dose can be administered in one or more administration. The precise determination of what would be considered an immunologically effective dose can be based on factors individual to each subject, including but not limited to the subject's age, size, and route of administration.

Numbering of amino acids, unless otherwise specified, is of amino acids comprising the RSV nonstructural protein 1 (NS1) of RSV strain A2 (SEQ ID NO: 1), or of an RSV NS1 protein having at least 95% sequence identity with SEQ ID NO: 1. The first amino acid (from the N-terminus) of RSV NS1 protein is designated amino acid 1. For example, S5 indicates the presence of serine at amino acid position 5 of the RSV NS1 protein. The notation Δ6-10, for example indicates a deletion of amino acids from and including amino acid L6 to and including amino acid K10.

DETAILED DESCRIPTION

In the following sections, various exemplary compositions and methods are described in order to detail various embodiments. Practicing the various embodiments does not require the employment of all or even some of the specific details outlined herein, but rather that concentrations, time, and other specific details may be modified through routine experimentation. In some cases, well known methods or components have not been included in the description Embodiments disclosed herein provide compositions, methods, and uses for respiratory syncytial viruses (RSV) and immunogenic compositions thereof. Certain embodiments provide RSV having a mutated NS1 protein, where the mutation causes the uncoupling of the NS1 protein's replication and type I interferon (IFN) antagonist functions. In some embodiments, this uncoupling can produce virions capable of inducing a strong, long-lasting innate immune response while maintaining its ability to replicate in vitro. Also provided are methods for amplifying RSV in host cells, wherein amplified RSV has mutated NS1 protein in which the protein's replication and IFN antagonistic functions are uncoupled. In certain embodiments, the amplified RSV having mutated NS1 protein is formulated into immunogenic compositions, including vaccines. Other embodiments provide methods for inducing an effective immune response against RSV infection in a subject.

The U.S. Food and Drug Administration has approved production of live, attenuated vaccines in host cell lines MRC-5, WI-38, and Vero. Both MRC-5 and WI-38 cell lines divide much less rapidly than do Vero cells, and produce lower virus yields. In addition, Vero cells do not produce interferon. Due in part to a higher growth rate of Vero cells, higher yield of RSV in Vero, and the lack of interferon response in Vero cells sets this cell line ahead of the other vaccine-producer cell line candidates.

It is known that people can be infected repeatedly throughout life with RSV, indicating that this virus does not induce strong protective immunity in an affected individual that is long-lasting. Induction of strong, long-lasting adaptive immunity requires strong innate immune activation. RSV nonstructural protein 1 (NS1) is a potent antagonist of the type I interferon (IFN) response, which is generally required for strong innate immune activation. It was previously demonstrated that deletion of the NS1 gene results in higher IFN production, providing evidence that NS1 plays a role in reduced IFN production. An RSV mutant lacking NS1 (ΔNS1) was found to be both highly attenuated and immunogenic in chimpanzees. However, deletion of NS1 significantly reduced virus yield in vitro, even in IFN-deficient cells lines such as Vero. For example, an RSV ΔNS1 deletion virus was demonstrated to replicate over 20-fold less than WT RSV in Vero cells. The dramatically reduced replication of the RSV ΔNS1 mutant reduces the economic viability of producing an RSV with an NS1 deletion, despite the favorable characteristics of such a mutation.

In certain embodiments, the replication function of RSV NS1 can be uncoupled from its IFN antagonistic activity. Uncoupling the replication function of RSV NS1 from its IFN antagonistic activity can result in the enhancement of virus production in Vero cells relative to RSV ΔNS1 and limits IFN antagonism by the virus. In some embodiments, deletion mutations near the N-terminus reduced or eliminated IFN antagonism. In certain embodiments, the NS1 mutant viruses disclosed herein can grow to higher titers than RSV lacking its entire NS1 gene (ΔNS1), demonstrating an uncoupling of the NS1 protein's replication and IFN antagonistic functions.

In certain embodiments, an RSV can include a mutated NS1 protein that supports RSV replication better than RSV ΔNS1 while reducing or eliminating the antagonism of IFN production relative to wild-type NS1. Reduction or elimination of IFN antagonism was demonstrated to permit a cell infected with this RSV to initiate an interferon response. As demonstrated in FIG. 3C, an RSV lacking the NS1 gene (ΔNS1) replicates about 100-fold less effectively than WT RSV in Vero cells. Recombinant RSVs (rRSV) including a mutated NS1 support virus replication in cells such as Vero cells, allowing peak virus titers to reach levels greater than those attainable by rRSV ΔNS1. In certain embodiments, the rRSV having a mutated NS1 protein reaches peak virus titer 10- to over 100-fold greater than that of rRSV ΔNS1. In one embodiment, an rRSV including a mutated NS1 protein reaches peak viral titer of at least 10-fold greater than that of rRSV ΔNS1. In another embodiment, an rRSV having a mutated NS1 protein reaches peak viral titer of at least 20-fold greater than that of rRSV ΔNS1.

Figure 3A:
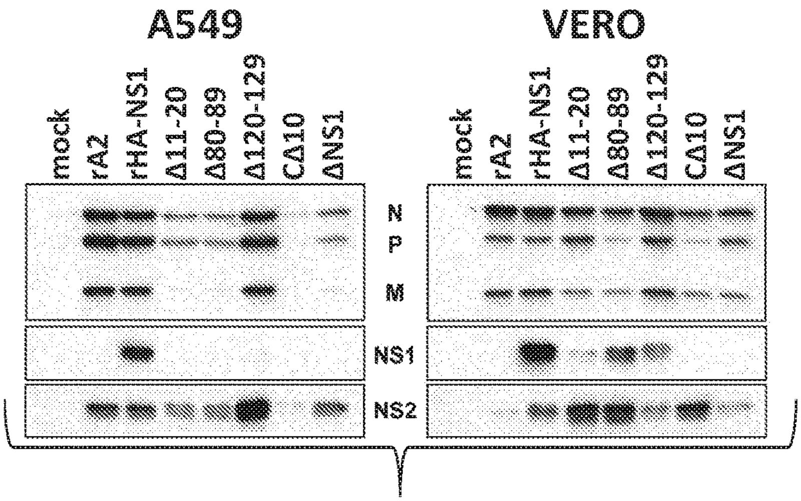
FIG. 3A are exemplary digital images of Western blots representing rRSV replication of NS1 10 aa deletion mutants in A549 (left) or Vero cells (right). RSV N, P and M proteins (top); NS1 protein (anti-HA, middle); and NS2 protein (bottom).
Figure 3B:
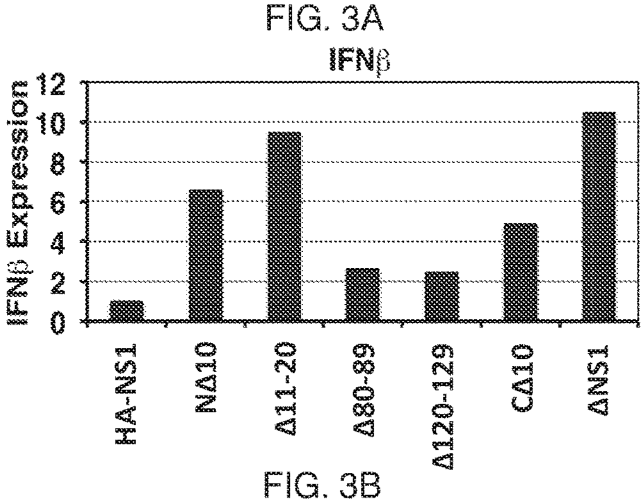
FIG. 3B is an exemplary bar graph representing IFNβ expression in A549 cells infected with rRSV comprising NS1 10 aa deletion mutants. Means of duplicate samples are presented.
Figure 5A:
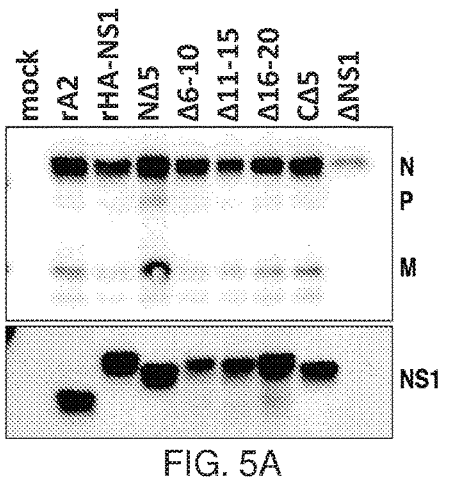
FIG. 5A are digital images of Western blots representing rRSV replication of the indicated NS1 5 aa deletion mutants in Vero cells. RSV N, P and M proteins (top) and NS1 protein (anti-HA, bottom).
Figure 5B:
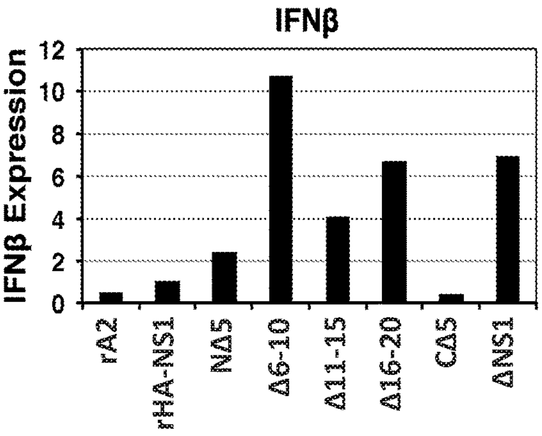
FIG. 5B is an exemplary bar graph representing IFNβ expression in A549 cells infected with rRSV comprising NS1 5 aa deletion mutants. Means of duplicate samples are presented.

In some embodiments, the mutated NS1 proteins of rRSV permit an infected cell to initiate an enhanced interferon response relative to wild-type NS1 by eliminating or at least decreasing NS1 protein's IFN antagonistic function. This is beneficial, as wild-type NS1 antagonizes IFN transcription (FIGS. 3B and 5B). When affected cells are able to initiate a suitable IFN response following infection by RSV, strong innate immune activation can occur, leading to induction of strong, long-lasting adaptive immunity to RSV infection in an individual.

In some embodiments, deletion mutations of one or more of the first 20 amino-terminal amino acids of RSV NS1 (aa 1-20) can uncouple or at least partially uncouple the protein's replication and IFN antagonistic properties. In other embodiments, one or more substitution mutations in the first 20 amino-terminal amino acids of RSV NS1 can uncouple or at least partially uncouple the protein's replication and IFN antagonistic properties. In yet other embodiments, a combination of deletion and substitution mutations in the first 20 amino-terminal amino acids of RSV NS1 can uncouple or at least partially uncouple the protein's replication and IFN antagonistic properties.

In some embodiments, 10 or more amino acids of the first 20 amino-terminal amino acids of RSV NS1 (aa 1-20) are deleted. In certain embodiments, 10 or more consecutive amino acids of the first 20 amino-terminal amino acids of RSV NS1 are deleted. In some embodiments, the amino acid deletions are not all consecutive, meaning that the deletion mutation can include consecutive and non-consecutive mutations of 10 or more amino acids. In certain embodiments, deletion mutations of 10 or more amino acids occurring in the first 20 amino-terminal amino acids of RSV NS1 can include, but are not limited to, deletion mutations NΔ10, Δ6-15, Δ6-18, Δ8-18, Δ8-20, Δ11-20, and Δ6-10,12,15-19. In certain embodiments, the RSV NS1 amino-terminal deletion mutation can be NΔ10 or Δ11-20. In some embodiments, the deletion mutants are relative to a polypeptide having an amino acid sequence at least 95% sequence identity with SEQ ID NO: 1. In other embodiments, the mutated NS1 proteins can have an amino acid sequence selected from SEQ ID NO: 2 (NΔ10), SEQ ID NO: 4 (Δ6-15), SEQ ID NO: 5 (Δ6-18), SEQ ID NO: 6 (Δ8-18), SEQ ID NO: 7 (Δ8-20), SEQ ID NO: 8 (Δ11-20), and SEQ ID NO: 9 (Δ6-10, 12, 15-19). Some embodiments provide a polynucleotide encoding a protein having the amino acid sequence of any one of SEQ ID NOs: 2 or 4-9.

In other embodiments, 7 or fewer amino acids from the first 20 amino-terminal amino acids of RSV NS1 (aa 1-20) are deleted. In certain embodiments, 7 or fewer consecutive amino acids of the first 20 amino-terminal amino acids are deleted. In other embodiments, the amino acid deletions are not all consecutive, meaning that the deletion mutation can include consecutive and non-consecutive mutations of 7 or fewer amino acids. In certain embodiments, deletion mutations of 7 or fewer amino acids occurring in the first 20 amino-terminal amino acids of RSV NS1 can include, but are not limited to, deletion mutations NΔ5, Δ2-5, Δ2-7, Δ5-7, Δ6-10, Δ11-15, Δ16-20, and Δ11-13,18-20. In certain embodiments, the RSV NS1 amino-terminal deletion mutation can be Δ6-10, Δ11-15, or Δ16-20. In other embodiments, the RSV NS1 amino-terminal deletion mutation can be Δ6-10. In some embodiments, the deletion mutants are relative to a polypeptide having an amino acid sequence at least 95% sequence identity with SEQ ID NO: 1. In other embodiments, the mutated NS1 proteins can have an amino acid sequence selected from SEQ ID NO: 10 (NΔ5), SEQ ID NO: 11 (Δ2-5), SEQ ID NO: 12 (Δ2-7), SEQ ID NO: 13 (Δ5-7), SEQ ID NO: 14 (Δ6-10), SEQ ID NO: 15 (Δ11-15), SEQ ID NO: 16 (Δ16-20) and SEQ ID NO: 17 (Δ11-13,18-20). Some embodiments provide a polynucleotide encoding a protein having the amino acid sequence of any one of SEQ ID NOs: 10-17.

In some embodiments, a single amino acid deletion within the first 20 amino-terminal amino acids of RSV NS1 (aa 1-20) can uncouple or at least partially uncouple the protein's replication and IFN antagonistic properties. The single amino acid deletion can be a deletion of any one of the first 20 amino-terminal amino acids of RSV NS1. In particular embodiments, single amino acid deletions in the first 20 amino-terminal amino acids of RSV NS1 can include, but are not limited to, deletion of residue 9, 11, 12, or 13. In a particular embodiment, amino acid 11 of NS1 is deleted, resulting in RSV NS1 mutant rRSV NS1Δ11. In some embodiments, the deletion mutants are relative to a polypeptide having an amino acid sequence at least 95% sequence identity with SEQ ID NO: 1. In other embodiments, the mutated NS1 proteins can have an amino acid sequence selected from SEQ ID NO: 19 (Δ9), SEQ ID NO: 20 (Δ11), SEQ ID NO: 21 (Δ12), and SEQ ID NO: 22 (Δ13). Some embodiments provide a polynucleotide encoding a protein having the amino acid sequence of any one of SEQ ID NOs: 19-22.

In other embodiments, small deletions of 2 to 3 amino acids from the first 20 amino-terminal amino acids of RSV NS1 can uncouple or at least partially uncouple the protein's replication and IFN antagonistic properties. In particular embodiments, small deletions in the first 20 amino-terminal amino acids of RSV NS1 can include, but are not limited to, deletion of residues 7 and 8 (Δ7,8), 9 through 11 (Δ9-11), and 9 and 12 (Δ9,12). In a particular embodiment, amino acids 9 and 12 of SEQ ID NO: 1 are deleted. In some embodiments, the deletion mutants are relative to a polypeptide having an amino acid sequence at least 95% sequence identity with SEQ ID NO: 1. In other embodiments, the mutated NS1 proteins can have an amino acid sequence selected from SEQ ID NO: 23 (Δ7,8), SEQ ID NO: 24 (Δ9-11), and SEQ ID NO: 25 (Δ9,12). Some embodiments provide a polynucleotide encoding a protein having the amino acid sequence of any one of SEQ ID NOs: 23-25.

In some embodiments, deletion mutations of one or more of the 10 carboxy-terminal amino acids of RSV NS1 (aa 130-139) can uncouple or at least partially uncouple the protein's replication and IFN antagonistic properties. In particular embodiments, one or more substitution mutations in the 10 carboxy-terminal amino acids RSV NS1 can uncouple or at least partially uncouple the protein's replication and IFN antagonistic properties. In yet other embodiments, a combination of deletion and substitution mutations in the 10 carboxy-terminal amino acids RSV NS1 can uncouple or at least partially uncouple the protein's replication and IFN antagonistic properties. In a particular embodiment the 10 carboxy-terminal amino acids of RSV NS1 (aa 130-139) are deleted (CΔ10). In another embodiment the 5 carboxy-terminal amino acids of RSV NS1 (aa 135-139) are deleted (CΔ5). In some embodiments, the deletion mutants can have an amino acid sequence of at least 95% sequence identity with SEQ ID NO: 1. In other embodiments, the mutated NS1 proteins can have an amino acid sequence represented by SEQ ID NO: 3 (CΔ10) or SEQ ID NO: 18 (CΔ5).

In certain embodiments, substitution of one or more amino acids of NS1, either alone or in combination with a deletion mutation described herein, can uncouple or at least partially uncouple NS1 protein's antagonistic activity from its replication function. One or more NS1 amino acids can be substituted by any amino acid capable of at least partially uncoupling the protein's IFN antagonism from its replication function. In some embodiments, charge and/or hydrophobicity at a particular amino acid location is maintained while promoting uncoupling of the replication and IFN antagonism functions of the protein. The substitution mutation allows a cell infected with RSV comprising the mutated NS1 protein to produce IFN and generate an innate immune response while also replicating adequately in vitro, allowing for the economical production of the recombinant virus. In some embodiment, one or more substitution mutations can be made at those amino acid positions described as targets for deletion mutations. In certain embodiments, NS1 mutations comprise a combination of deletion and substitution mutations.

Mutations disclosed herein can be achieved by any method known in the art such as, for example, PCR site directed mutagenesis Other embodiments described herein provide methods for uncoupling NS1 protein's IFN antagonistic property from its replication function. Amino acids capable of eliminating or at least partially relieving the protein's antagonism of IFN expression in an infected cell while at the same time having no or only a moderate effect on the ability of an rRSV to replicate in vitro can be identified by, for example, scanning deletion mutation analysis, scanning substitution mutation analysis, bioinformatics analysis, and combinations thereof. Identified amino acids can be referred to as "uncoupling amino acids," as they at least partially uncouple NS1's IFN antagonistic function from its replication function.

In certain embodiments, bioinformatics analysis can be used to predict the location of one or more functional NS1 protein sequences or even single amino acids. Results from such an analysis can then be used to guide scanning mutation analysis. Mutations of uncoupling amino acid candidates can then be scanned for effects on IFN antagonism using a reporter assay, such as that described in Example 1. Mutations in the NS1 protein that relieve NS1 antagonism of IFN expression can then be tested for their effect on in vitro RSV replication. Successful uncoupling mutations can be considered as those mutations that eliminate or at least partially relieve the protein's antagonism of IFN expression in an infected cell while at the same time having no or only a moderate effect on the ability of an rRSV comprising the candidate uncoupling mutation to replicate in vitro. An rRSV with reduced IFN antagonism with the ability to replicate well in vitro will be a prime candidate for use as a live attenuated RSV in an immunogenic composition.

Other embodiments provide a live, attenuated RSV including a mutated NS1 protein, wherein the mutation at least partially uncouples the NS1 protein's replication function from its IFN antagonistic properties. In some embodiments, RSV having a mutated NS1 with uncoupled replication and IFN antagonism functions can act as a backbone for attenuating mutations. In other embodiments, a live, attenuated RSV virus can be mutated to have the NS1 with uncoupled replication and IFN antagonism functions as described herein. Live, attenuated RSV viruses do not cause vaccine-associated enhanced RSV disease. Rather, they can broadly stimulate innate, humoral, and cellular immunity both systemically and locally in the respiratory tract, they can be delivered intranasally, and they replicate in the upper respiratory tract of young infants despite the presence of passively acquired, maternally-derived RSV neutralizing antibody. By mutating the RSV NS1 protein as provided by the embodiments described herein and incorporating the mutated NS1 protein into a live, attenuated RSV, or mutating the RSV NS1 protein of a live attenuated RSV to a protein having uncoupled replication and IFN antagonism functions, a live attenuated RSV capable of inducing strong, long-lasting adaptive immunity to RSV can be efficiently and economically amplified in Vero cells. Because of the uncoupling, IFN antagonism by the mutated NS1 is reduced or nearly eliminated relative to wild-type NS1, and is able to replicate to peak titers higher than those attainable when NS1 is completely removed. In some embodiments, an RSV comprising a mutated NS1 protein with uncoupled replication and IFN antagonism functions can attain a peak viral titer 10- to over 100-fold greater than that of rRSV ΔNS1. This improvement in attainable virus titer can make production of immunogenic compositions including live attenuated RSV capable of producing strong, long-lasting adaptive immunity, such as vaccines, more economical.

In certain embodiments, a live, attenuated RSV is modified to incorporate a mutation of the NS1 protein as provided by the embodiments described herein. The NS1 protein of any live, attenuated RSV can be so mutated. For example, the NS1 protein of RSV ΔNS2 Δ1313 I1314L, Lot RSV #005A, RSV LID ΔM2-2, and MEDI-559, which are in clinical trials as vaccines, can be modified to improve viral replication in RSV including NS1 capable of inducing strong, long-lasting adaptive immunity. It is contemplated herein than any other live attenuated RSV can be mutated as described herein. In certain embodiments, modification of the NS1 protein of a live, attenuated RSV as described herein can improve the replication and thus peak virus titer of live, attenuated RSV virions in Vero cells relative to live, attenuated RSV lacking the NS1 protein (RSV ΔNS1), which is capable of producing a strong adaptive immune response, but replicates poorly.

In other embodiments, an RSV having a mutated NS1 protein can be further modified so as to attenuate the virus and produce a live attenuated RSV with uncoupled replication and IFN antagonism functions. Any attenuating mutation can be incorporated into the RSV having a mutated NS1 with uncoupled replication and IFN antagonism functions. Attenuating mutations can include, but are not limited to those mutations found in RSV ΔNS2 Δ1313 I1314L, Lot RSV #005A, RSV LID ΔM2-2, and MEDI-559. Other attenuation strategies can include, but are not limited to mutations, in a zinc-binding motif of the M2-1 protein, which improves both immunogenicity and attenuation of a live attenuated RSV vaccine, or mutations in the methyltransferase domain of the large (L) polymerase protein, which attenuates RSV, and mutations in the G protein, which improves production efficiency of live attenuated RSV up to 10-fold in vitro.

In some embodiments, two or more attenuating strategies can be combined to produce a live attenuated RSV vaccine having good immunogenicity and capable of inducing long-lasting adaptive immunity to RSV while also capable of being efficiently and economically amplified.

In certain embodiments, replication of RSV capable of producing a strong, long-lasting adaptive immune response is improved by uncoupling the replication function of RSV NS1 protein from its IFN antagonistic function. Improvement is relative to RSV amplified in Vero cells where RSV lacks NS1 (RSV ΔNS1).

Certain embodiments provide methods for amplifying a mutant RSV disclosed herein. Methods for amplifying an RSV can include providing a cell culture of Vero cells, inoculating the cell culture of Vero cells with an RSV having a mutated NS1 protein with uncoupled replication and IFN antagonism functions as described herein, incubating the cell culture with the RSV, and harvesting RSV virus following the incubation period. In some embodiments, the RSV having a mutated NS1 protein with uncoupled replication and IFN antagonism functions is a live, attenuated RSV. General parameters for growing Vero cells and amplification of RSV in Vero cells are described in the Methods, and are known to those of skill in the art. Routine modifications to adapt these methods to a situation are within the scope of the present disclosure (e.g., cell culture conditions, inoculation and incubation times, inoculum titer, harvesting methods, etc.)

In some embodiments, HEp-2 (or similar) cells can be transfected with a plasmid having a cDNA copy of the RSV RNA genome having a mutant NS1 gene including mutations that uncouple the NS1 protein's replication and IFN antagonistic functions. These cells can be cotransfected with plasmids encoding the four viral proteins required for RSV mRNA transcription an RSV genome replication: the nucleocapsid (N) protein; the phosphoprotein (P); the large (L) polymerase protein; and the M2-1 transcription enhancer protein. All of these plasmids contain a T7 promoter and T7 polymerase is provided by a recombinant virus, plasmid or cell line expressing T7 polymerase. These cells produce recombinant (r) RSV that replicate in many cell types, without the need for the initiating plasmids. The rRSV can be passaged several times in cultured cells to produce high-titered seed stocks for testing and for initiating production of immunogenic compositions (e.g., vaccines).

In certain embodiments, the method for amplifying an RSV includes a purifying step in which harvested RSV is purified. Purification of the harvested RSV can be carried out by any method for virus purification known in the art.

In other embodiments, RSV including an NS1 protein with uncoupled replication and IFN antagonism functions can be formulated into an immunogenic composition against RSV. In some embodiments, the immunogenic composition against RSV can be a pharmaceutical composition, such as a vaccine.

In certain embodiments, an immunogenic composition against RSV can include an RSV harvested following amplification using a method described herein. In some embodiments, the harvested RSV can have an NS1 protein wherein the protein's replication and IFN antagonistic functions are uncoupled as a result of a mutation described herein. In some embodiments, the immunogenic composition against RSV includes a live attenuated RSV. In certain embodiments, the immunogenic composition against RSV can include one or more pharmaceutically acceptable carriers, vehicles, excipients, or any combination thereof. Suitable pharmaceutical carriers, vehicles, and excipients for formulating a pharmaceutically acceptable immunogenic compound, including vaccines, are known in the art. In some embodiments, the immunogenic composition can include at least one adjuvant for further induction of the immune system in a subject when administered.

Other embodiments provide methods for inducing an effective immune response against RSV in a subject. In some embodiments, the method can include administering an immunologically effective dose of an immunogenic composition against RSV described herein. In certain embodiments, the subject can be a human subject. In some embodiments, the subject can be a human infant or child. The immunogenic composition against RSV can be administered to a subject at risk of acquiring an RSV infection, or a subject having an RSV infection, including a subject having a recurrent infection. Accordingly, certain embodiments provide methods for preventing an RSV infection comprising administering an immunogenic composition described herein.

In certain embodiments, methods for inducing an effective immune response against RSV can reduce the incidence of, or probability of, recurrent RSV infection or RSV disease in a subject. In other embodiments, an immunogenic composition against RSV can be administered to a patient post-infection, thereby protecting them from subsequent RSV infections or ameliorating the symptoms from subsequent infections.

In some embodiments, a subject is administered at least one immunologically effective dose subsequent to an initial dose. The immunogenic composition against RSV can be administered to the subject once, or can be administered a plurality of times, e.g., one, two, three, four, or five times.

In certain embodiments, immunogenic compositions against RSV can be administered to a subject in a convenient manner, for example, subcutaneously, intravenously, by oral administration, inhalation, intradermally, transdermal application, intravaginal application, topical application, intranasally, or by rectal administration. In one embodiment, an immunologically effective dose of an immunogenic composition against RSV can be administered to a human infant intranasally. In other embodiments, the route of administration can be intradermal administration or oral administration.

In some embodiments, an immunogenic composition can be administered to a subject in an appropriate pharmaceutically acceptable carrier or diluent, co-administered with enzyme inhibitors or in an appropriate carrier such as liposomes. As used herein, the term "pharmaceutically acceptable carrier" includes diluents such as saline and aqueous buffer solutions. Dispersions can also be prepared in glycerol, liquid polyethylene glycols, and mixtures thereof and in oils. Under ordinary conditions of storage and use, these preparations may contain a preservative to prevent the growth of microorganisms or other stabilizing formulation.

Pharmaceutical compositions suitable for injectable use can be administered by means known in the art. For example, sterile aqueous solutions (where water soluble) or dispersions and sterile powders for the extemporaneous preparation of sterile injectable solutions or dispersion can be used. In all cases, the composition can be sterile and can be fluid to the extent that easy syringability exists. It can be stable under the conditions of manufacture and storage and can be preserved against the contaminating action of microorganisms such as bacteria and fungi. The pharmaceutically acceptable carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of microorganisms can be achieved by heating, exposing the agent to detergent, irradiation or adding various antibacterial or antifungal agents.

Sterile injectable solutions can be prepared by incorporating active compound (e.g. a compound that induces an immune response to RSV) in the required amount in an appropriate solvent with one or a combination of ingredients enumerated above, as required, followed by filtered sterilization.

Upon formulation, solutions will be administered in a manner compatible with the dosage formulation and in such amount as is immunologically effective. The formulations are easily administered in a variety of dosage forms, such as the type of injectable solutions described above. It is contemplated that compositions are especially suitable for intramuscular, subcutaneous, intradermal, intranasal and intraperitoneal administration.

In another embodiment, nasal solutions or sprays, aerosols or inhalants can be used to deliver the immunogenic composition of interest. Additional formulations that are suitable for other modes of administration include suppositories and pessaries.

Certain formulations can include excipients, for example, pharmaceutical grades of mannitol, lactose, starch, magnesium stearate, sodium saccharine, cellulose, magnesium carbonate and the like.

A pharmaceutical composition can be prepared with carriers that protect active ingredients against rapid elimination from the body, such as time-release formulations or coatings. Such carriers include controlled release formulations, such as, but not limited to, microencapsulated delivery systems, and biodegradable, biocompatible polymers, such as ethylene vinyl acetate, polyanhydrides, polyglycolic acid, polyorthoesters, polylactic acid and others are known.

EXAMPLES

The materials, methods, and embodiments described herein are further defined in the following Examples. Certain embodiments are defined in the Examples herein. It should be understood that these Examples, while indicating certain embodiments, are given by way of illustration only. From the disclosure herein and these Examples, one skilled in the art can ascertain the essential characteristics of this disclosure, and without departing from the spirit and scope thereof, can make various changes and modifications to adapt it to various usages and conditions.

Example 1—Identification of IFN Antagonistic Regions in NS1 Protein

In one exemplary method, to identify regions of the NS1 protein important for IFN antagonism, an IFN induction reporter assay was established based on IFN expression pathways. Overexpression of the N-terminal CARD domain of RIG-1 (N-RIG-I) or MAVS results in activation of the RIG-I-like helicase (RLH) pathway leading to activation of interferon regulatory factor 3 (IRF3) directed transcription. Overexpression of the TRIF adaptor molecule activates the Toll-like receptor 3 (TLR3) pathway, also leading to IRF3 activation. Using reporter gene constructs for IRF3-responsive promoters (IFNβ-luc and ISG56-luc), NS1 co-expression was found to inhibit transcription activated by both the RLH and the TLR3 pathways (FIG. 1).

In certain exemplary methods, using the IFN induction reporter assay, a series of deletion mutations in the RSV NS1 protein were tested to identify those mutations that had lost their ability to inhibit IRF3 activation. These experiments identified NS1 protein regions involved in IFN antagonism.

Figure 2A:
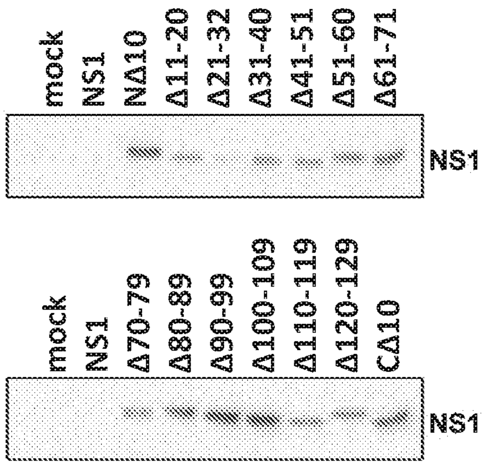
FIGS. 2A-2B are exemplary digital images of Western blots illustrating protein stability of NS1 deletion mutants. HEK293T cells were transfected with expression plasmids encoding WT or mutant HA-NS1 either alone (FIG. 2A) or in combination with HA-NS2 expression plasmid (FIG. 2B).
Figure 2B:
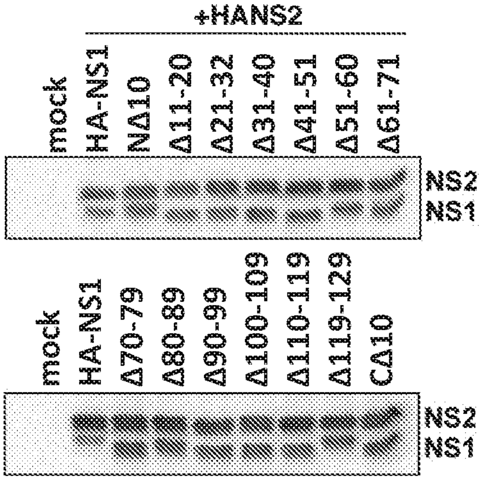
Figure 2C:
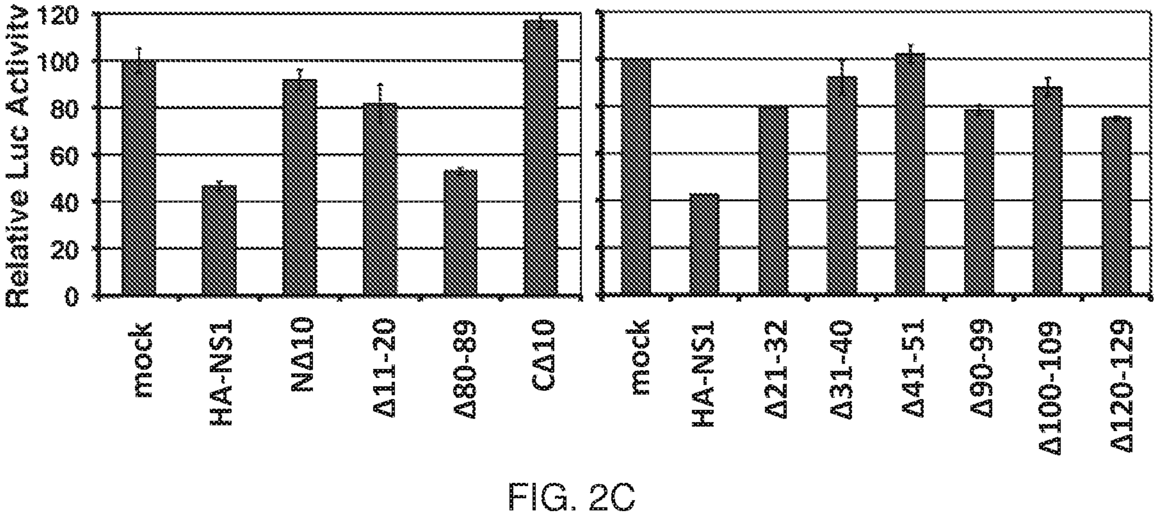
FIG. 2C is an exemplary bar graph representing interferon antagonism of the indicated NS1 deletion mutants. Shown are means±SEM of triplicate samples.

Large (≥10 aa) deletions in NS1 were made and tested by transient expression. Deletion mutations included: NΔ10 (deletion of first 10 aa from the N-terminus); Δ11-20; Δ21-32; Δ31-40; Δ41-51; Δ51-60; Δ61-71; Δ70-79; Δ80-89; Δ90-99; Δ100-109; Δ100-119; Δ120-129; and CΔ10 (deletion of last 10 aa from the C-terminus). All of the large deletions tested reduced protein stability (FIG. 2). However, co-expression of NS2 with the NS1 large deletion mutants resulted in the stabilization of specific cellular and viral proteins, including the mutant NS1 proteins (FIG. 2*b*). This result confirmed that while the mutant NS1 proteins had been produced, they were being degraded in the absence of NS2. The large deletion mutation analysis identified the N-terminal 20 and C-terminal 10 amino acids of NS1 as important for inhibition of MAVS-mediated IFN activation. Large deletions of internal sequences, such as amino acids 79-89, had less of an effect (FIG. 2C), although this finding does not preclude the possibility that a smaller deletion, a single amino acid deletion, or one or more amino acid mutations in the internal NS1 protein sequence would be effective.

The ability of select large deletion NS1 mutants to inhibit IFN transcription in the context of viral infection was tested. The wild-type (WT) NS1 gene in a full-length, antigenomic cDNA was replaced with the most stable large deletion NS1 mutants (FIG. 2A). A series of recombinant RSV (rRSV) comprising the large deletion NS1 mutations were rescued. The NS1 protein produced by all of these mutant viruses included an N-terminal HA-tag to enable detection of the NS1 protein. A549 and Vero cells infected with the rRSVs (input multiplicity of infection (MOI) of 3) expressed different levels of viral proteins N, P, and M (FIG. 3A, right top), demonstrating different levels of virus replication among the large deletion mutants. In all cases, a smaller amount of NS1 was present relative to the amount of the N, P, and M proteins in cells infected with RSV expressing a mutant NS1 protein compared to the control rHA-NS1 RSV (FIG. 3, right middle), showing that the NS1 mutants were less stable than the control NS1 protein.

To determine the level of IFNβ induced by RSV comprising large deletion mutations in NS1, A549 cells were infected (MOI of 3) and IFNβ mRNA was quantified using real-time PCR (QPCR). Despite their greatly reduced NS1 expression levels, rHA-NS1Δ80-89 and rHA-NS1Δ120-129 mutant viruses both inhibited IFNβ induction to near wild-type levels, indicating that the level of WT NS1 produced in RSV infection is in excess of the level required for IFNβ antagonism (FIG. 3B). NS1 mutant rRSV with deletions of the N-terminal 10 aa (NΔ10), amino acids 11 to 20 (Δ11-20), and the C-terminal 10 aa (CΔ10) of NS1 resulted in higher IFNβ production, showing a loss of some or all of the NS1 mutant rRSV's ability to antagonize IFNβ production. This result shows the importance of the N- and C-termini for the IFN antagonism function of NS1.

Example 2—Replication of NS1 Large Deletion Mutations

Figure 3C:
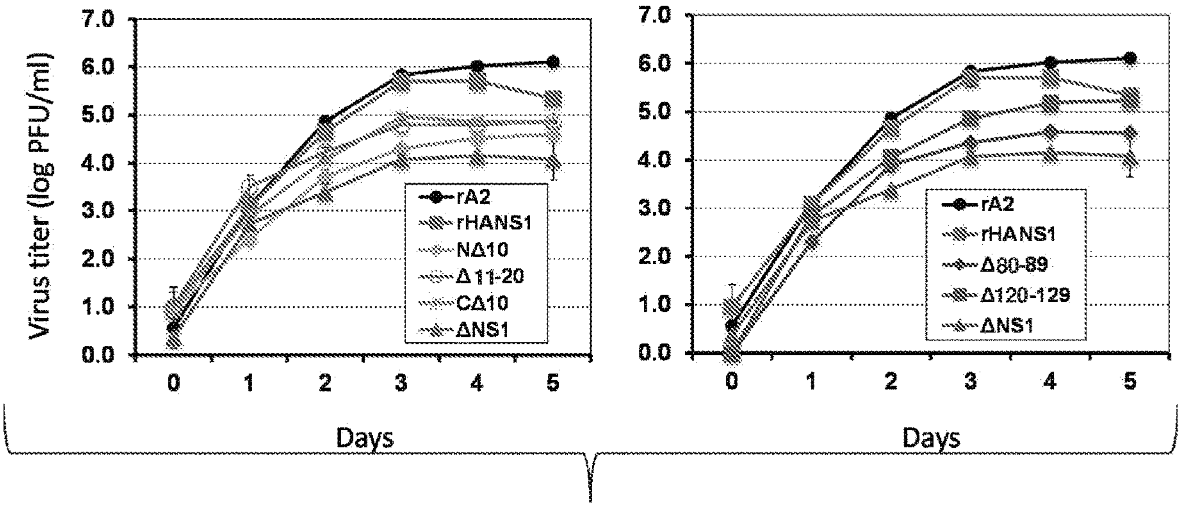
FIG. 3C includes two line graphs representing viral titers of RSV comprising NS1 10 aa deletion mutants grown in Vero cells. The means±SEM of triplicate samples are presented.

In another exemplary method, RSV having large deletion mutations in NS1 were evaluated for their ability to replicate in Vero cells. Vero cells are IFN-deficient due to a genetic deletion of the Type I IFN genes from these cells. Attenuating effects on virus replication caused by IFN are thus diminished when using this cell line as a host for viral replication. In addition, Vero cells are certified for producing live attenuated vaccines, and are capable of producing high yields of RSV. Multiple step replication in Vero cells (MOI of 0.01) of rHA-NS1Δ80-89 and rHA-NS1Δ120-129, which were able to inhibit IFNβ transcription, was markedly decreased compared to WT rHA-NS1 (1.1 and 0.5 log PFU lower peak viral titer, respectively) (FIG. 3C). The rRSV carrying NS1 genes with large deletions that were unable to inhibit IFNβ transcription—rHA-NS1 NΔ10, rHA-NS1 Δ11-20, and rHA-NS1 CΔ10—also replicated to lower levels than rHA-NS1 (control rRSV) (1.1, 0.9, and 0.8 log PFU lower peak viral titer, respectively), but significantly higher than ΔNS1 (0.4, 0.6, and 0.7 log PFU higher peak viral titer, respectively) (FIG. 3C, left). These data show that there are several regions of NS1 that participate in RSV replication, and that at least some of these regions are distinct from those involved in IFN antagonism.

Example 3—Predictive Identification of NS1 Functional Domains

Figure 4:
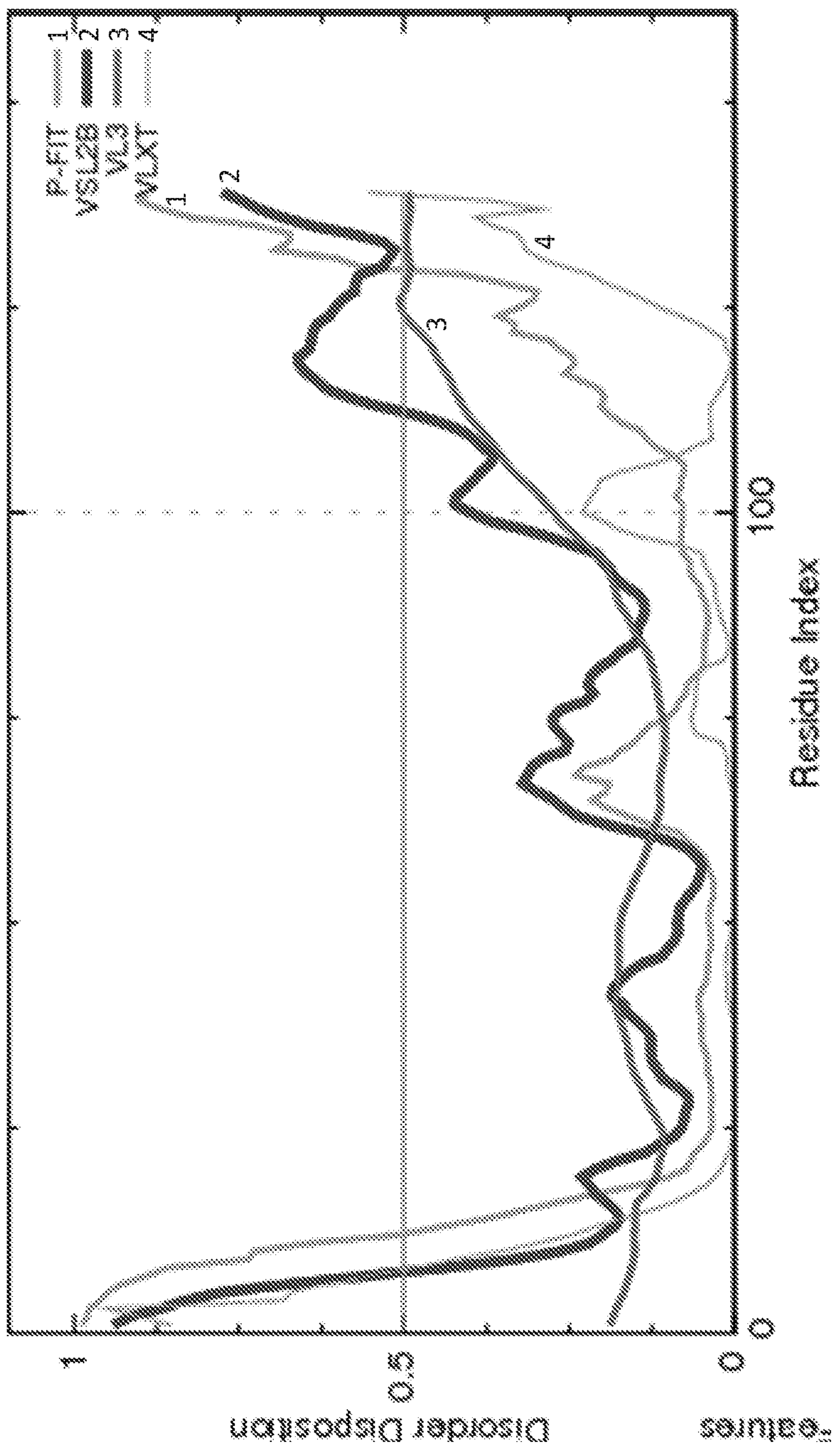
FIG. 4 is a plot representing structural disorder in regions of RSV NS1

Analysis of primary and secondary NS1 protein structure features was performed. A disordered region within a protein is often an indication of a functional domain. Regions in NS1 that are most likely to be disordered were identified using 4 different disorder prediction algorithms (see for example: DisProt; see Sickmeier M, Hamilton J A, LeGall T, Vacic V, Cortese M S, Tantos A, Szabo B, Tompa P, Chen J, Uversky V N, Obradovic Z, Dunker A K. 2006. "DisProt: the Database of Disordered Proteins." Nucleic Acids Res. 2007 January; 35 (Database issue):D786-93. Epub 2006 Dec. 1). The identified regions are positioned in the N- and C-termini (FIG. 4), which correlates with the large deletion mutations described above. The plot of FIG. 4 indicates structural disorder in regions of RSV NS1, as deduced by PONDR, VSL2B, VLS, and VLXT (DisProt; see Sickmeier M, Hamilton J A, LeGall T, Vacic V, Cortese M S, Tantos A, Szabo B, Tompa P, Chen J, Uversky V N, Obradovic Z, Dunker A K. 2006. "DisProt: the Database of Disordered Proteins." Nucleic Acids Res. 2007 January; 35 (Database issue): D786-93. Epub 2006 Dec. 1).

Figure 5C:
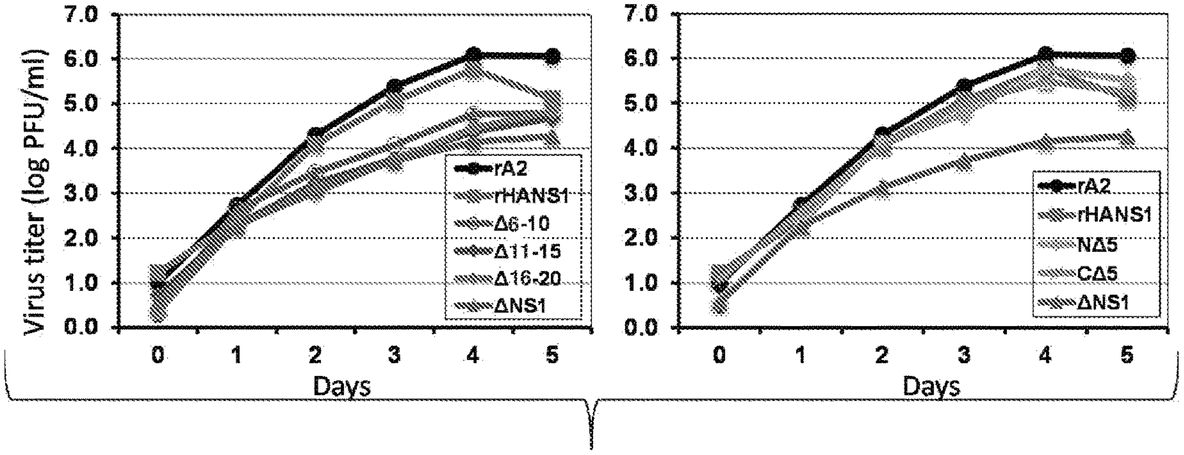
FIG. 5C includes two line graphs representing viral titers of rRSV comprising NS1 5 aa deletion mutants grown in Vero cells. The means±SEM of triplicate samples are presented.

Example 4—Narrowing the IFN Antagonistic Functional Sequences of NS1 Protein To further hone in on the minimal length sequences necessary for IFN antagonism and for replication support, NS1 mutant rRSV with 5 amino acid (aa) deletions in the N- and C-terminal regions were produced. The small deletion mutations generated herein included: NΔ5; Δ6-10; Δ11-15; Δ16-20; and CΔ5. The mutated NS1 proteins produced by the rRSVs were as stable as the wild-type NS1 protein produced by rHA-NS1 RSV in Vero cells (FIG. 5A), in contrast to the 10 aa deletion mutants, which were unstable to varying degrees. NS1 mutant rRSV with 5 aa deletions between amino acids 5-20 induced IFNβ mRNA in A549 cells, indicating that the mutations relieved the IFN antagonism caused by wild-type NS1 (FIG. 5*b*). The rHA-NS1Δ6-10 mutant rRSV induced the highest level of IFNβ mRNA expression. Infection of Vero cells (MOI 0.01) with the rRSV having the small deletion NS1 mutations resulted in peak virus titers intermediate between rHA-NS1 and ΔNS1. rHA-NS1Δ6-10 RSV peak titer levels were approximately 0.7 log PFU/ml greater than ΔNS1 and 1 log PFU/ml lower than the wild-type control rHA-NS1 (FIG. 5C, left). rHA-NS1Δ11-15 RSV and rHA-NS1Δ16-20 RSV reached peak titers comparable to rHA-NS1Δ6-10. The small deletion mutants that displayed WT IFN antagonism (NΔ5 and CΔ5) replicated similarly to rHA-NS1 (FIG. 5C, right). These data show that several residues between amino acids 5-20 are important for the IFN antagonism of NS1, with amino acids 5-10 being particularly important.

Example 5—Single Amino Acid Deletion NS1 Mutations

Figure 6:
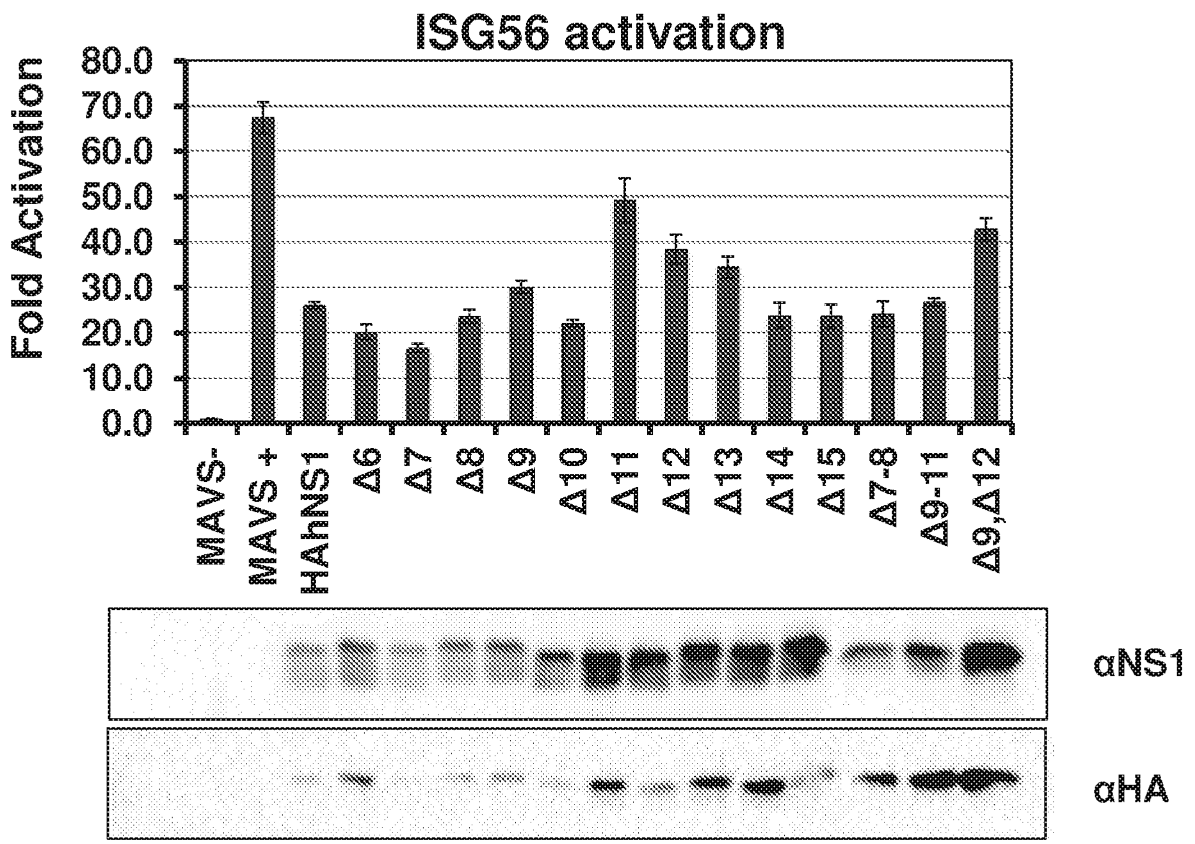
FIG. 6 is an exemplary bar graph (top) representing interferon inhibition by single and combination amino acid deletion NS1 mutants in a 293T transfection assay, and a corresponding digital image of a Western blot (bottom).
Figure 7A:
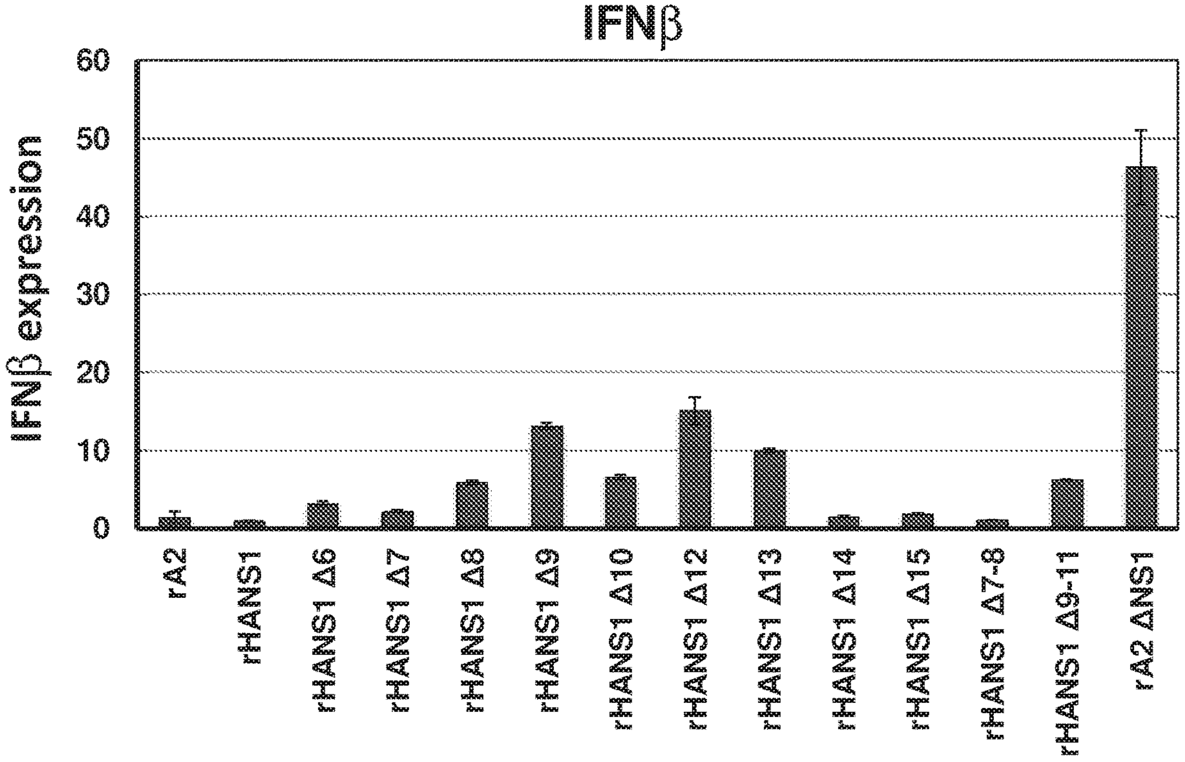
FIGS. 7A-7B are exemplary bar graphs representing IFNβ expression induction by single and combination amino acid deletion NS1 mutants in A549 cells.
Figure 7B:
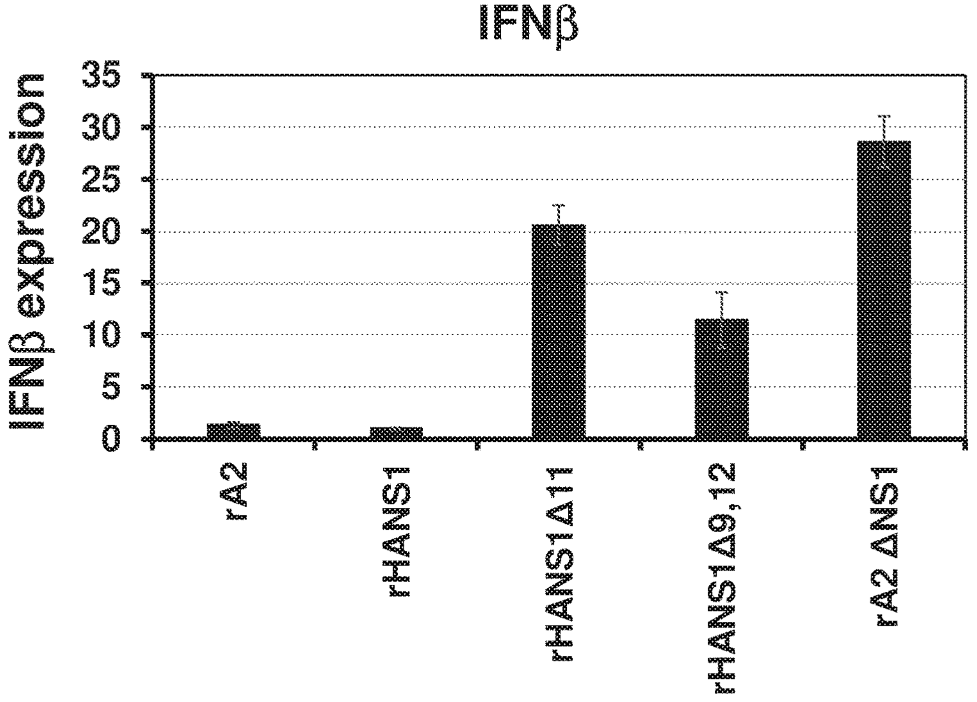

As demonstrated herein, using 10 and 5 amino acid (aa) NS1 deletion mutants suggested that most of the interferon (IFN) antagonist activity of RSV NS1 is encoded in the N-terminal 15 aa of the protein. NS1 mutants having single aa deletions from residues 6 through 15 were generated and tested for IFN antagonism in the transfection assay (FIG. 6) and in the context of recombinant RSV (rRSV) (FIGS. 7A and 7B). Deletion of residues 11, 12, or 13 alone was sufficient to decrease IFN antagonism in the transfection assay (FIG. 6). Deletion of residues 12 or 13 in rRSV NS1 also resulted in a significant decrease in IFN antagonism, as evidenced by the increased IFNβ mRNA induction. Interestingly, deletion of residue 9 showed a comparable decrease in IFN antagonism in the context of rRSV but not in the transfection assay. Deletion of residue 11 in rRSV NS1 resulted in a significant reduction in the mutant's ability to inhibit IFN induction (FIG. 7B).

Example 6—Combination Amino Acid Deletion NS1 Mutations

In addition to the single amino acid deletions, certain combination mutants were constructed. Deletions of residues 7 and 8 (Δ7,8) or 9 through 11 (Δ9-11) did not appear to impair IFN antagonism in the transfection assay (FIG. 6). Recombinant RSV encoding the Δ7,8 deletion mutation also had little effect, in contrast to the Δ9-11 mutant, which induced IFNβ mRNA levels comparable to the MO mutant and slightly lower than the Δ9 mutant. Based on the results of the single aa deletion rRSV (FIG. 7), combination mutants were produced, including a Δ9,12 mutant. Both the Δ9 and Δ12 single deletion rRSV exhibited enhanced IFN induction in A549 cells; however, only the Δ12 mutant has decreased antagonism of MAVS-induced ISG56 activation in the 293T transfection assay. The Δ9,12 mutant exhibited similar levels of MAVS inhibition compared with the Δ12 single mutant. Deletion of residues 9 and 12 in rRSV did not appear to have an additive effect on the mutant's ability to inhibit IFN induction (see FIGS. 7A and 7B).

Example 7—Materials and Methods

Plasmids. The NS1 expression plasmid (pcDNA5-NS1) was provided but can be generated by any method known in the art. Primers encoding an HA tag were inserted into the BamHI site at the 5' end of the ORF, destroying the upstream BamHI site. Deletion mutants were constructed using PCR mutagenesis with a high fidelity enzyme (e.g. DeepVent, New England Biolabs). The expression plasmids encoding N-RIG-I, MAVS, and TRIF were provided. The firefly luciferase reporter constructs for the IFNβ and ISG56 promoters were obtained.

IFN induction assay. HEK293T cells were transfected with expression plasmids for the IFN inducers (N-RIG-I, MAVS, TRIF) plus either the IFNβ-luc (IFNβ promoter followed by the firefly luciferase gene) or ISG56-luc (ISG56 promoter followed by the firefly luciferase gene) in the presence or absence of NS1 plasmid. phRL-TK (e.g. Promega), expressing the Renilla luciferase gene under the control of the HSV-TK promoter, was used as a transfection control. Cells were harvested 24 h post-transfection and subjected to the Dual Luciferase assay (Promega).

Construction of recombinant RSV. The shuttle vector consisting of the 5' end of the antigenome through the middle of the N gene (pGEM-NS, Tran et al. 2007, Virology 368:73-82) was modified to contain an HA tag at the 5' end of the NS1 ORF followed by a BamHI site and a NotI site at the 3' end of the NS1 ORF. WT and mutant NS1 from the pcDNA5 expression plasmids were inserted into the modified pGEM-NS. These NS1 mutant pGEM-NS plasmids were digested with AatII/AflII and inserted into the AatII/AflII window of pGEM-AX. The resultant mutant pGEM-AX plasmids were then digested with AatII/AvrII and the inserts were cloned into the full-length RSV antigenome cDNA (D53) digested with AatII/AvrII. All mutants were sequenced to confirm the presence of the mutations and absence of adventitious mutations. Two independent clones of each mutant D53 were used for virus recovery (Hotard et al. 2012, Virology 434:129). BSR-T7/3 cells were transfected with expression plasmids encoding codon-optimized versions of RSV N, P, M2-1, and L plus each D53 mutant using GeneJuice (Novagen). Three days post-transfection, the cells were passaged. Upon the appearance of cytopathic effect, the supernatant was harvested, clarified, and used to infect Vero cells to produce a master seed stock. All working stocks were derived from this master seed stock.

Western blot assay. Whole cell extracts were harvested at 24 h post-transfection or infection and subjected to SDS-PAGE. Protein was transferred to nitrocellulose membranes and probed with rabbit antiserum to RSV N), P and M (NS1 and NS2), or commercial antibodies to STAT2 and HA. Western blots were developed using secondary anti-mouse or anti-rabbit IgG conjugated to horseradish peroxidase (KPL) and chemiluminescence (Millipore). Images were captured using the ChemiDoc gel documentation system (e.g. BioRad).

Quantitative PCR. Total RNA was extracted from infected cells 20 h p.i. by RNAzol, per the manufacturer's instructions (Molecular Research Center). 500 ng of RNA was used for first-strand cDNA synthesis using iScript (e.g. BioRad). Quantitative PCR was performed using 1 μl of cDNA per 25 μl PCR reaction in a 96 well plate by SensiFast qPCR mix (e.g. Bioline) in a Chromo4 qPCR machine (BioRad). Primers for IFNβ (Forward: CTAACTGCAACCTTTCGAAGC (SEQ ID NO: 26); Reverse: GGAAAGAGCTGTAGTGGAGAAG (SEQ ID NO: 27)) and 18S rRNA as a control (Forward: GTAACCCGTTGAACCCCATT (SEQ ID NO: 28); Reverse: CCATCCAATCGGTAGTAGCG (SEQ ID NO: 29)).

All of the compositions and methods disclosed and claimed herein can be made and executed without undue experimentation in light of the present disclosure. While the compositions and methods have been described in terms of particular embodiments, it is apparent to those of skill in the art that variations maybe applied to the compositions and methods and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

The invention claimed is:

1. A mutant respiratory syncytial virus (RSV) comprising a mutated nonstructural protein 1 (NS1) comprising an amino acid deletion in the first 20 amino acids of an amino-terminus of the NS1, the amino acid deletion in the first 20 amino acids of the amino-terminus of the NS1 consisting of a mutation selected from the group consisting of Δ6-15; Δ6-18; Δ8-18; Δ8-20; Δ6-10,12,15-19; NΔ5; Δ2-5; Δ2-7; Δ5-7; Δ6-10; Δ11-15; Δ11-13,18-20; Δ9; Δ11; Δ12; Δ13; Δ7,8; Δ9-11; and Δ9, 12 of an RSV NS1 protein having at least 95% sequence identity with SEQ ID NO: 1.

2. The mutant RSV of claim 1, further comprising at least one substitution mutation in the 20 amino-terminal amino acids (aa 1-20) or 10 carboxy-terminal amino acids of the RSV NS1 protein.

3. The mutant RSV of claim 1, wherein the deletion mutation is selected from the group consisting of Δ6-10; Δ11; and Δ9,12.

4. The mutant RSV of claims 1, 2 or 3, wherein the mutant RSV is an attenuated RSV.

5. An immunogenic composition against RSV comprising the attenuated RSV according to claim 4 and a pharmaceutically acceptable excipient.

6. A method for producing an immunogenic composition against respiratory syncytial virus (RSV) comprising:

providing a cell culture of host cells;

inoculating the cell culture of host cells with the mutant RSV of claim 1;

incubating the cell culture of host cells with the mutant RSV;

harvesting RSV following the incubation step; and formulating the harvested RSV into an immunogenic composition against RSV.

7. The method of claim 6, further comprising purifying the harvested RSV.

8. The method of claim 6, wherein formulating comprises combining the harvested RSV with a pharmaceutically acceptable carrier, vehicle, or excipient, and adjuvant, or a combination thereof.

9. The method of claim 6, wherein the immunogenic composition against RSV comprises a pharmaceutically acceptable carrier, vehicle, or excipient, an adjuvant, or a combination thereof.

10. An immunogenic composition against RSV produced by a method comprising:

providing a cell culture of host cells;

inoculating the cell culture of host cells with the mutant RSV of claim 1;

incubating the cell culture of host cells with the mutant RSV;

harvesting RSV following the incubation step; and formulating the harvested RSV into an immunogenic composition against RSV.

11. A method for inducing an effective immune response against respiratory syncytial virus (RSV) infection in a subject, comprising administering to the subject an immunologically effective dose of an immunogenic composition against RSV according to claim 5.

12. The method of claim 11, wherein the subject is human.

13. The method of claim 11, wherein the subject is a human infant or child.

14. The method of claim 11, wherein the immunogenic composition against RSV is administered via an administration route comprising intranasal administration; subcutaneous administration; intramuscular administration; intradermal administration; and oral administration.

15. The method of claim 11, further comprising administering at least one subsequent immunologically effective dose of the immunogenic composition against RSV.

* * * * *

UNITED STATES PATENT AND TRADEMARK OFFICE
CERTIFICATE OF CORRECTION

| | |
|---|---|
| PATENT NO. | : 10,947,512 B2 |
| APPLICATION NO. | : 15/752548 |
| DATED | : March 16, 2021 |
| INVENTOR(S) | : Mark Edward Peebles et al. |

It is certified that error appears in the above-identified patent and that said Letters Patent is hereby corrected as shown below:

In the Specification

At Column 1, Line 15, please insert the following paragraph, immediately after the section titled, "CROSS REFERENCE TO RELATED APPLICATIONS":
-- GOVERNMENT LICENSE RIGHTS
This invention was made with government support under R01 AI081977 awarded by the National Institutes of Health. The government has certain rights in the invention. --

Signed and Sealed this
Fourth Day of July, 2023

Katherine Kelly Vidal
*Director of the United States Patent and Trademark Office*